(12) United States Patent
Gunther et al.

(10) Patent No.: US 11,998,366 B2
(45) Date of Patent: Jun. 4, 2024

(54) GENERATING A BREATHING ALERT

(71) Applicant: Nutrits, Ltd., Ramat-Gan (IL)

(72) Inventors: Jacob Gunther, North Logan, UT (US); Nathan E. Ruben, Smithfield, UT (US)

(73) Assignee: Nutrits, Ltd., Ramat-Gan (IL)

( * ) Notice: Subject to any disclaimer, the term of this patent is extended or adjusted under 35 U.S.C. 154(b) by 3 days.

(21) Appl. No.: 17/862,266

(22) Filed: Jul. 11, 2022

(65) Prior Publication Data

US 2022/0361824 A1 Nov. 17, 2022

Related U.S. Application Data

(63) Continuation of application No. 16/828,479, filed on Mar. 24, 2020, now Pat. No. 11,389,119, which is a continuation-in-part of application No. 15/697,220, filed on Sep. 6, 2017, now Pat. No. 10,709,354.

(60) Provisional application No. 62/383,769, filed on Sep. 6, 2016.

(51) Int. Cl.
| | |
|---|---|
| *G06T 7/00* | (2017.01) |
| *A61B 5/00* | (2006.01) |
| *A61B 5/08* | (2006.01) |
| *A61B 5/107* | (2006.01) |
| *G06T 7/13* | (2017.01) |
| *G06T 7/143* | (2017.01) |
| *G06T 7/194* | (2017.01) |
| *G06T 7/44* | (2017.01) |

(52) U.S. Cl.
CPC ............ *A61B 5/743* (2013.01); *A61B 5/0816* (2013.01); *A61B 5/107* (2013.01); *A61B 5/4815* (2013.01); *A61B 5/4818* (2013.01); *A61B 5/7264* (2013.01); *A61B 5/741* (2013.01); *A61B 5/746* (2013.01); *A61B 5/747* (2013.01); *G06T 7/0012* (2013.01); *G06T 7/13* (2017.01); *G06T 7/143* (2017.01); *G06T 7/194* (2017.01); *G06T 7/44* (2017.01); *G06T 2207/10016* (2013.01); *G06T 2207/20076* (2013.01); *G06T 2207/30088* (2013.01)

(58) Field of Classification Search
None
See application file for complete search history.

(56) References Cited

U.S. PATENT DOCUMENTS

| | | | |
|---|---|---|---|
| 4,273,596 | A | 6/1981 | Gutierrez et al. |
| 6,352,517 | B1 | 3/2002 | Flock et al. |
| 8,792,969 | B2 | 7/2014 | Bernal et al. |
| 9,852,507 | B2 | 12/2017 | Gunther et al. |

(Continued)

OTHER PUBLICATIONS

Tarassenko et al., Non-contact video-based vital sign monitoring using ambient light and auto-regressive models. Physiol Meas. May 2014;35(5), pp. 807-831. doi: 10.1088/0967-3334/35/5/807.*

*Primary Examiner* — Guillermo M Rivera-Martinez
(74) *Attorney, Agent, or Firm* — Kunzler Bean & Adamson

(57) ABSTRACT

For generating a breathing alert is disclosed, a method receives a video stream of a subject. The method further estimates a breathing signal from the video stream. The method determines one of a large-scale motion and/or a breathing event of the subject based on the breathing signal. The method generates an alert if both no breathing event is identified and no large-scale motion of the subject is identified within an event time interval.

15 Claims, 34 Drawing Sheets

(56) References Cited

U.S. PATENT DOCUMENTS

| | | | |
|---|---|---|---|
| 2009/0226043 A1* | 9/2009 | Angell | G16H 50/80 707/999.107 |
| 2010/0063419 A1* | 3/2010 | Mostafavi | A61B 5/1135 600/587 |
| 2011/0251493 A1 | 10/2011 | Poh et al. | |
| 2011/0305388 A1 | 12/2011 | Wedi et al. | |
| 2012/0289850 A1 | 11/2012 | Xu et al. | |
| 2013/0035599 A1* | 2/2013 | De Bruijn | A61B 5/1135 600/476 |
| 2013/0342670 A1 | 12/2013 | Kyal et al. | |
| 2014/0029824 A1 | 1/2014 | Shi et al. | |
| 2014/0275832 A1* | 9/2014 | Muehlsteff | A61B 5/7278 600/301 |
| 2015/0094606 A1* | 4/2015 | Mestha | A61B 5/7282 600/534 |
| 2015/0245787 A1* | 9/2015 | Kyal | A61B 5/1128 600/476 |
| 2015/0324636 A1 | 11/2015 | Bentley et al. | |
| 2015/0332457 A1* | 11/2015 | Mestha | G06T 7/254 382/103 |
| 2015/0342535 A1* | 12/2015 | Chen | A61B 5/024 600/476 |
| 2016/0089041 A1 | 3/2016 | Keat et al. | |
| 2016/0106340 A1* | 4/2016 | Mestha | A61B 5/746 600/476 |
| 2016/0174887 A1 | 6/2016 | Kirenko et al. | |
| 2016/0210747 A1* | 7/2016 | Hay | G06F 3/04847 |
| 2016/0239632 A1 | 8/2016 | Yu et al. | |
| 2016/0343135 A1* | 11/2016 | De Haan | A61B 5/02416 |
| 2016/0371833 A1* | 12/2016 | Prasad | A61B 5/4818 |
| 2017/0042488 A1 | 2/2017 | Muhsin | |
| 2017/0119304 A1* | 5/2017 | Jeanne | A61B 5/1135 |
| 2017/0213438 A1* | 7/2017 | Peng | G06T 7/0012 |
| 2017/0238842 A1* | 8/2017 | Jacquel | A61B 5/0205 |
| 2017/0354330 A1* | 12/2017 | Kaiser | A61N 5/1049 |
| 2017/0367651 A1* | 12/2017 | Tzvieli | A61B 5/0075 |
| 2019/0029604 A1 | 1/2019 | Jones et al. | |
| 2019/0034713 A1* | 1/2019 | Fraz | A61B 5/1128 |
| 2019/0209052 A1* | 7/2019 | Jeanne | A61B 5/7246 |

* cited by examiner

165

| Breath Rate 231 |
| Maximum Inter-Breath Interval 233 |
| Minimum Inter-Breath Interval 235 |
| Inter-Breath Interval Statistics 237 |
| Inter-Breath Interval Histogram 239 |
| Apnea Event Data 241 |
| Breathing Signal 183 |

160

| Motion Frequency 243 |
| Motion Magnitude 245 |
| Motion Duration 247 |
| Sleep Length 249 |
| Sleep Quality 251 |
| Sleep Intervals 253 |
| Sleep Position 341 |
| Sleep Status 343 |

| Pixel 9 | Pixel Weight 11 |
|---|---|
| Pixel 9 | Pixel Weight 11 |

⋮

| Pixel 9 | Pixel Weight 11 |
|---|---|
| Region Sum 277 ||
| Scalar Time Signal 271 ||
| Low Order Subspace Decompostion 273 ||
| Decomposition Frequency 275 ||

Logistic Regression Classifier
281

Breathing Model
283

Crying Model
285

Smiling Model
287

Smiling Image
289

Notification
291

Position Model
293

Sleep Model
295

CPAP Model
297

Device Database
299

| D Energy Signal |
| --- |
| 311 |

| D[1]/D[2] Average Signal |
| --- |
| 313 |

| D[3]/D[4] Average Signal |
| --- |
| 315 |

| Y[1]/Y[2] SRSS |
| --- |
| 317 |

| Y[3]/Y[4] SRSS |
| --- |
| 319 |

| Output Probability |
| --- |
| 318 |

320

| Pixel 9 | Mask Value 321 |
| Pixel 9 | Mask Value 321 |
| ⋮ | |
| Pixel 9 | Mask Value 321 |

325

| Pixel 9 | Color Value 327 | Probability Transform 329 |
| Pixel 9 | Color Value 327 | Probability Transform 329 |
| ⋮ | | |
| Pixel 9 | Color Value 327 | Probability Transform 329 |

Skin Histogram 326

```
┌─────────────────────────┐
│     Kernel Matrix       │
│          330            │
└─────────────────────────┘

┌─────────────────────────┐
│      Mean Vector        │
│          331            │
└─────────────────────────┘

┌─────────────────────────┐
│    Background Signal    │
│          333            │
└─────────────────────────┘

┌─────────────────────────┐
│ Background Signal Filter│
│          335            │
└─────────────────────────┘
```

GENERATING A BREATHING ALERT

CROSS-REFERENCE TO RELATED APPLICATIONS

This application is a continuation application that claims priority to U.S. patent application Ser. No. 16/828,479 entitled "GENERATING A BREATHING ALERT" and filed on Mar. 24, 2020 for Jacob Gunther, which is incorporated by reference, which is a continuation-in-part application of and claims priority to "U.S. patent application Ser. No. 15/697,220 entitled "GENERATING A BREATHING ALERT" and filed on Sep. 6, 2017 for Jacob Gunther, which is incorporated herein by reference, and which claims priority to U.S. Provisional Patent Application No. 62/383,769 entitled "IDENTIFYING A BREATHING EVENT" and filed on Sep. 6, 2016 for Jacob Gunther, which is incorporated by reference.

FIELD

The subject matter disclosed herein relates to breathing and more particularly relates to generating an alert.

BACKGROUND

Description of the Related Art

It is often desirable to determine if a subject is breathing.

BRIEF SUMMARY

A method for generating a breathing alert is disclosed. The method receives a video stream of a subject. The method further estimates a breathing signal from the video stream. The method determines one of a large-scale motion and/or a breathing event of the subject based on the breathing signal. The method generates an alert if both no breathing event is identified and no large-scale motion of the subject is identified within an event time interval.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which:

FIG. 2E is a schematic block diagram illustrating one embodiment of a frame region;

FIG. 2F is a schematic block diagram illustrating one embodiment of system data;

DETAILED DESCRIPTION

Figure 1A:
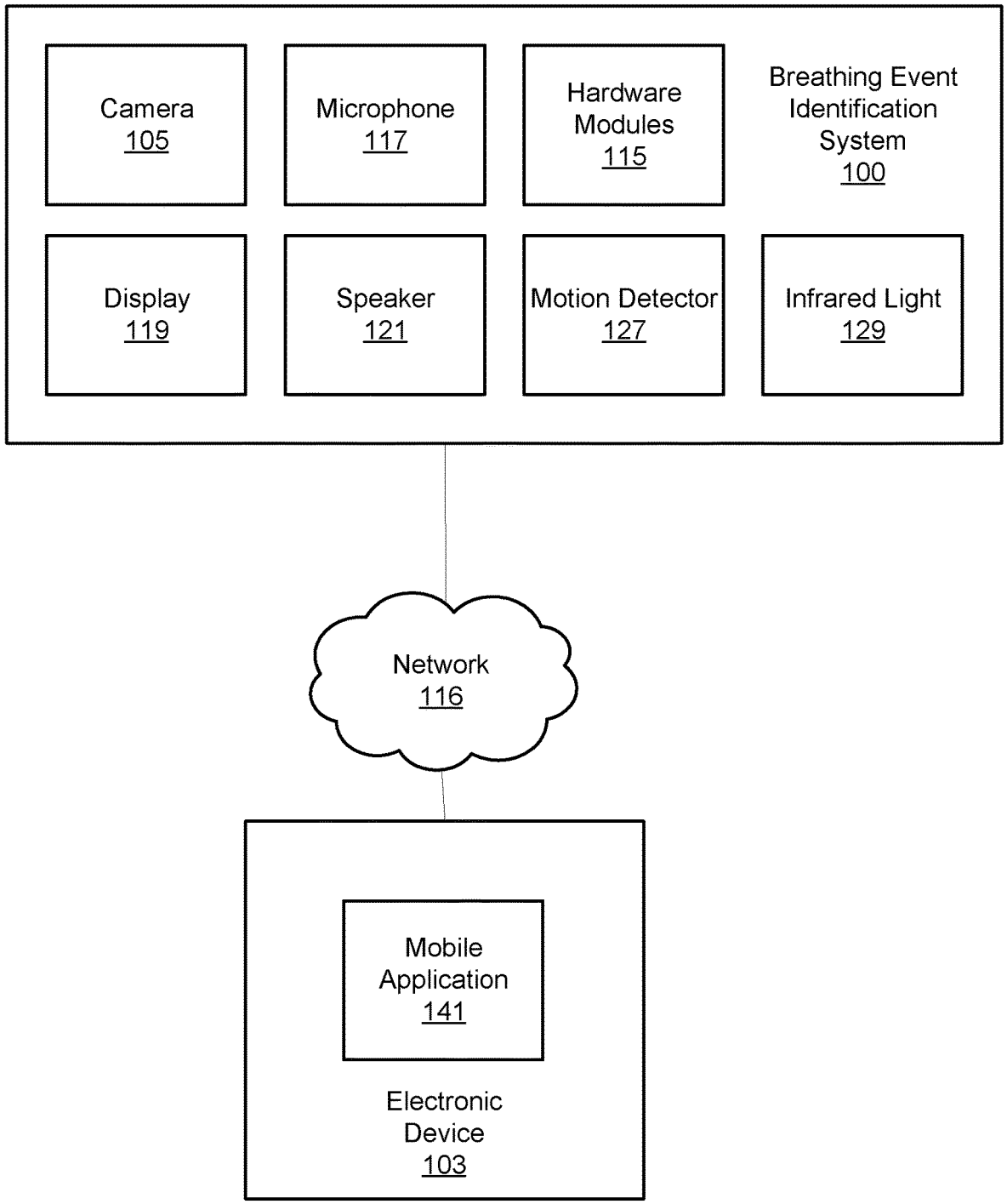
FIG. 1A is a schematic block diagram illustrating one embodiment of a breathing event identification system.

As will be appreciated by one skilled in the art, aspects of the embodiments may be embodied as a system, method or program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage medium storing machine readable code, computer readable code, and/or program code, referred hereafter as code. The computer readable storage medium may be tangible, non-transitory, and/or non-transmission. The computer readable storage medium may not embody signals. In a certain embodiment, the storage devices only employ signals for accessing code.

The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, R, Java, Java Script, Smalltalk, C++, C sharp, Lisp, Clojure, PHP, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise. The term "and/or" indicates embodiments of one or more of the listed elements, with "A and/or B" indicating embodiments of element A alone, element B alone, or elements A and B taken together.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. These code may be provided to a processing apparatus of a general purpose computer, special purpose computer, or other programmable data processing apparatus to produce a machine, such that the instructions, which execute via the processing apparatus of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, other programmable data processing apparatus, or other devices to cause a series of operational steps to be performed on the computer, other programmable apparatus or other devices to produce a computer implemented process such that the code which execute on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and program products according to various embodiments. In this regard, each block in the schematic flowchart diagrams and/or schematic block diagrams may represent a module, segment, or portion of code, which comprises one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

FIG. 1A is a schematic block diagram illustrating one embodiment of a breathing event identification system 100. The system 100 may identify a breathing event and/or large-scale motion for a subject from a video stream of the subject captured by a camera 105. In addition, the system 100 may generate an alert if no breathing event is identified and/or no large-scale motion is identified.

When a subject 110 may be at risk for ceasing to breathe, it is advantageous to monitor the subject 110 and identify the breathing rate and/or detect the cessation of breathing so that timely aid may be given. It is further advantageous to employ noninvasive monitoring to identify breathing events so the subject 110 is not disturbed.

Breathing events may be detected optically and audibly. For example, baby monitors may be used to monitor a baby's breathing through a video (sequence of images) of the baby captured by a camera 105 and/or a sound of the baby's breathing captured by a microphone 117. Unfortunately, when identifying breathing events, the consequences of both false positives and false negatives is so high that monitoring must detect breathing events with extreme accuracy.

In the depicted embodiment, the system 100 includes the camera 105, the microphone 117, hardware modules 115, a display 119, a speaker 121, a motion detector 127, and/or an infrared light 129. The system 100 may communicate with a network 116. In one embodiment, the system 100 communicates through the network 116 with a mobile application 141 residing on an electronic device 103. The network 116 may include the Internet, a mobile telephone network, a Wi-Fi network, a local area network, or combinations thereof. The electronic device 103 may be a mobile telephone, a tablet computer, a laptop computer, a computer workstation, or the like.

In one embodiment, the hardware modules 115 comprise dedicated semiconductor circuits. The dedicated semiconductor circuits may include a memory and a processing apparatus. In addition, the hardware modules 115 may comprise a computer.

The embodiments described herein identify breathing events and/or large-scale motions based on a video stream as will be described hereafter. The embodiments further generate alerts, present displays, present reports, and present statistics based on the breathing events and/or large-scale motion.

Figure 1B:
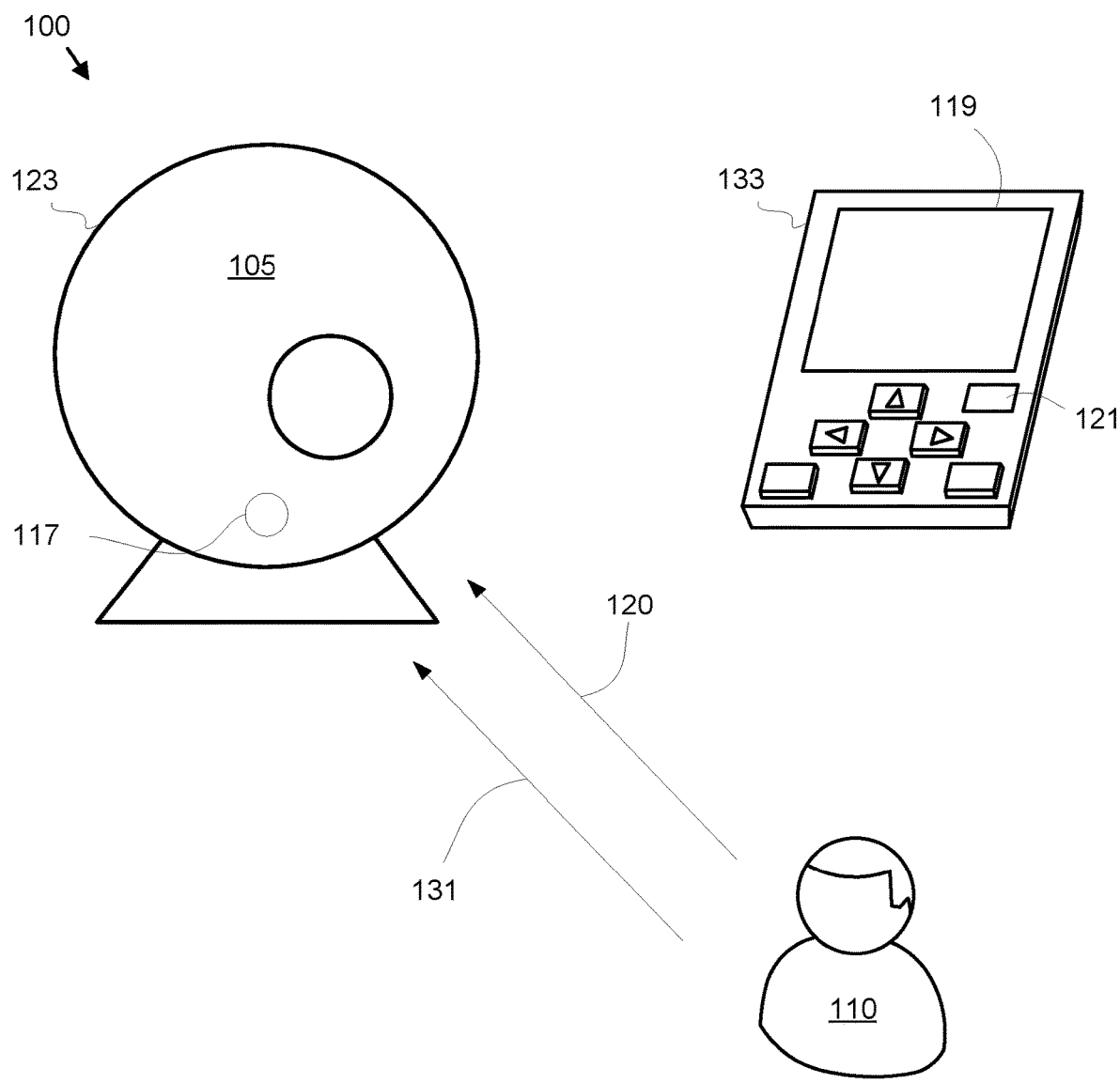
FIG. 1B is a drawing illustrating one embodiment of a breathing event identification system.

FIG. 1B is a drawing illustrating one embodiment of the breathing event identification system 100. In the depicted embodiment, the system 100 includes a monitor device 123 and a base station 133. The monitor device 123 may include the camera 105, the microphone 117, the hardware modules 115 (not shown), and the motion detector 127. The base station 133 may include the hardware modules 115 (not shown), the display 119 and/or the speaker 121. The monitor device 123 and the base station 133 may communicate through a wired connection, a wireless connection, and/or the network 116.

The camera 105 may capture a video stream 120 of the subject 110. In a certain embodiment, the video stream 120 comprises an infrared signal of a face of the subject 110. The camera 105 may employ a bandpass filter in the range of 0.8-2.5 micrometers. In addition, the camera 105 may employ Charge Coupled Device (CCD) that is tuned to 1.5 micrometers. The video stream 120 may be encoded using H.264 and/or 11265 encoding as defined by the Motion Picture Expert Group. The camera 105 may capture the video stream 120 as infrared image frames. The microphone 117 may capture an audio stream 131 from the subject 110. The audio stream 131 may be encoded using G711 encoding as defined by the International Telecommunications Union and/or ACC encoding as defined by the International Organization for Standards. In an alternate embodiment, the monitor device 123 and the base station are integrated in a single device.

In one embodiment, the video stream 120 and/or audio stream 131 are processed by the camera 105. In a certain embodiment, the video stream 120 and/or audio stream 131 are communicated to the base station 133 and processed by the base station 133. The video stream 120 and/or audio stream 131 may be recorded in a Motion Picture Expert Group-4 (MP4) container as defined by the Motion Picture Expert Group. The MP4 container may be communicated from the camera 105 to the base station 133.

The camera 105, the base station 133, and/or the mobile application 141 may maintain regular communications. In one embodiment, the camera 105, the base station 133, and/or the mobile application 141 may maintain continuous communications. Any of the camera 105, the base station 133, and/or the electronic device 103 executing a mobile application 141 may broadcast a request for communications. In one embodiment, the request is a User Datagram Protocol (UDP) request that is broadcast on a specific port. Alternatively, the request may be a Transmission Control Protocol (TCP) request. Other devices may listen for the request and communicator response with the unique identifier. For example, the camera 105 may communicate a UDP request. The base station 133 may receive the UDP request and respond with a response beacon that includes the unique identifier for the base station 133. The camera 105 may subsequently communicate with the base station 133.

In one embodiment, a device database may store network addresses for the camera 105, the base station 133, and/or the electronic device 103. The device database may be used to establish communications between the camera 105, the base station 133, and/or the electronic device 103. The base station 133 may notify the mobile application 141 if communication with the camera 105 is lost.

Figure 1C:
FIG. 1C is a schematic block diagram illustrating one embodiment of a breathing data.

FIG. 1C is a schematic block diagram illustrating one embodiment of a breathing data 165. The breathing data 165 may be organized as a data structure in a memory. In the depicted embodiment, the breathing data 165 includes a breath rate 231, a maximum inter-breath interval 233, a minimum inter-breath interval 235, inter-breath interval statistics 237, an inter-breath interval histogram 239, apnea event data 241, and the breathing signal 183.

The breath rate 231 may represent a frequency of breathing. The maximum inter-breath interval 233 may specify a longest interval between breathing events. The minimum inter-breath interval 235 may specify a shortest interval between breathing events. The inter-breath interval statistics 237 may specify one or more of a mean, average, and mode of intervals between breathing events. The inter-breath interval histogram 239 may describe the relative frequencies of breath intervals between breathing events. The breath intervals may be organized into one or more ranges.

The apnea event data 241 may be calculated from the breath rate 231, maximum inter-breath interval 233, minimum inter-breath interval 235, inter-breath interval statistics 237, and inter-breath interval histogram 239. The apnea event data 241 may be used to identify sleep apnea events.

The breathing signal 183 may be determined from the video stream 120 and/or the audio stream 131 as will be described hereafter.

Figure 1D:
FIG. 1D is a schematic block diagram illustrating one embodiment of a motion report.

FIG. 1D is a schematic block diagram illustrating one embodiment of a motion report 160. The motion report 160 maybe organized as a data structure in a memory. In the depicted embodiment, the motion report 160 includes a motion frequency 243, a motion magnitude 245, a motion duration 247, a sleep length 249, a sleep quality 251, sleep intervals 253, a sleep position 341, and a sleep status 343.

The motion frequency 243 may describe the frequency of large-scale motions by the subject 110. The motion magnitude 245 may describe a number of pixels affected by each motion. The motion duration 247 may describe the duration from start to end of each large-scale motion by the subject 110.

The sleep length 249 may describe a length of a time interval during which the subject 110 is asleep. The sleep quality 251 may estimate the restfulness of the sleep for the subject 110. The sleep intervals 253 may describe each interval during which the subject 110 is quietly asleep.

The sleep position 341 may describe positions of the head, body, and/or limbs of the subject 110. In addition, the sleep position 341 may describe an overall position. In one embodiment, the sleep position 341 comprises thrashing, a stomach orientation, a back orientation, and/or a side orientation.

The sleep status 343 may describe the sleep of the subject 110. The sleep status 343 may comprise one of asleep and awake. In addition, the sleep status 343 may comprise deep sleep, rapid eye movement (REM) sleep, and/or fitful sleep.

Figure 1E:
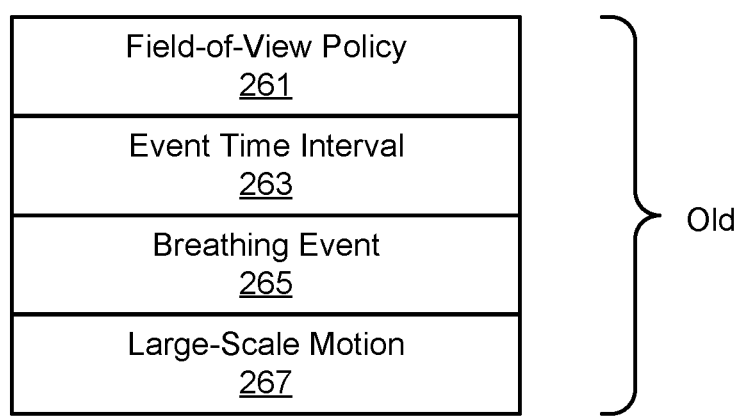
FIG. 1E is a schematic block diagram illustrating one embodiment of breathing data.

FIG. 1E is a schematic block diagram illustrating one embodiment of breathing data. The breathing data maybe organized as a data structure in a memory. In the depicted embodiment, the breathing data includes a field of view policy 261, an event time interval 263, a breathing event 265, and a large-scale motion 267.

The field of view policy 261 may specify when the subject 110 can be satisfactorily viewed by the camera 105. The event time interval 263 may specify a time interval during which a breathing event 265 or a large-scale motion 267 of the subject 110 must be identified in order to not generate an alert. The breathing event 265 may be an identified breath by the subject 110. The large-scale motion 267 may indicate motion by the subject 110. The motion may make determining a breathing event 265 difficult and/or impossible.

Figure 2A:
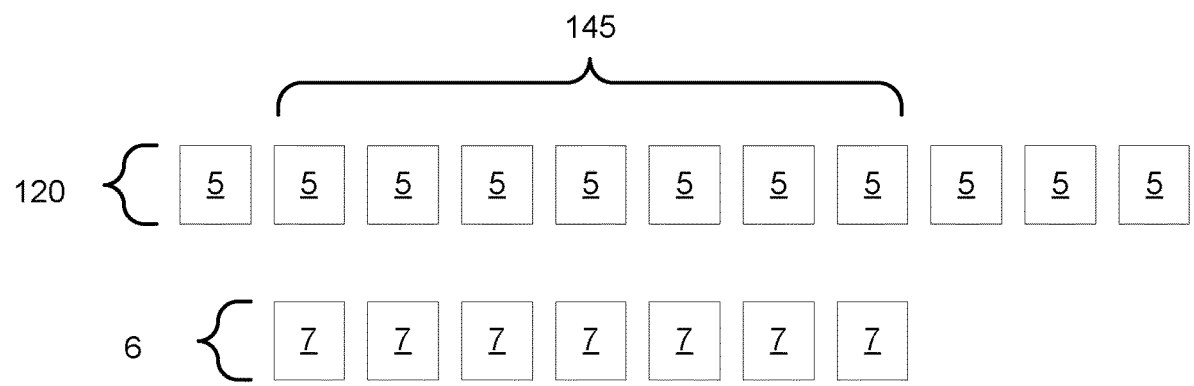
FIG. 2A is a schematic diagram illustrating one embodiment of video stream data.

FIG. 2A is a schematic diagram illustrating one embodiment of the video stream 120. In the depicted embodiment, the video stream 120 comprises a plurality of image frames 5. A time series 6 may be extracted from the video stream 120. The time series 6 may be from a windowed video subsequence 145. The time series 6 may be a vector time series 6. In one embodiment, background signals, non-moving objects, and/or a mean of the image frames 5 are removed to form removed frames 7 as will be described hereafter.

Figure 2B:
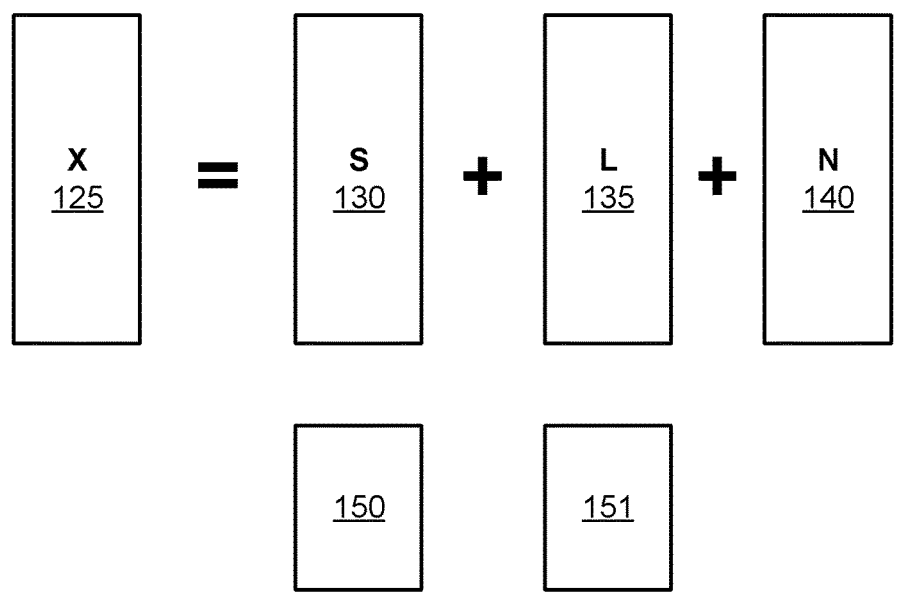
FIG. 2B is a schematic diagram illustrating one embodiment of sparse matrix calculation.

FIG. 2B is a schematic diagram illustrating one embodiment of sparse matrix S 130 calculation. In one embodiment, a matrix X 125 is generated from the time series 6. The time series 6 may be extracted from the windowed video subsequence 145 of the video stream 120 as the sequence I(t−N+1), I(t−N+2), I(t−N+3), . . . , I(t−2), I(t−1), I(t), where N is the length of the windowed video subsequence 145. The process 101 may organize the windowed video sequence 145 into a matrix X 125. In one embodiment, X 125 is an M by N matrix, and may include M rows and N columns.

In one embodiment, M is calculated as a product of a height of an image frame 5 of the video stream 120 in pixels, a width of the image frame 5 of the video stream 120 in pixels, and a number of channels in the image frames of the video stream 120. As a result, the matrix X 125 may be organized as a plurality of vectors with a vector for each image frame I in the windowed video sequence 145. The organization of the matrix X 125 greatly simplifies and enhances the calculation of the breathing event 265.

The matrix X 125 may be decomposed into a sparse matrix S 130 representing moving objects and a low rank matrix L 135 representing non-moving objects 151 as will be described hereafter. In one embodiment, the decomposition of matrix X 125 includes an additive noise matrix N 140.

In one embodiment, matrix S 130 is calculated as S=X-L and/or S=X-L-N. Moving objects 150 may be reconstructed from the sparse matrix S 130. In one embodiment, each pixel of the reconstructed video stream of moving objects 150 comprises a scaler time series. Alternatively, each pixel of the reconstructed video stream of moving objects 150 includes a vector time series. In one embodiment, a sliding sparse subsequence 155 that corresponds to the windowed video sequence 145 is extracted from the video stream of moving objects 150.

Figure 2C:
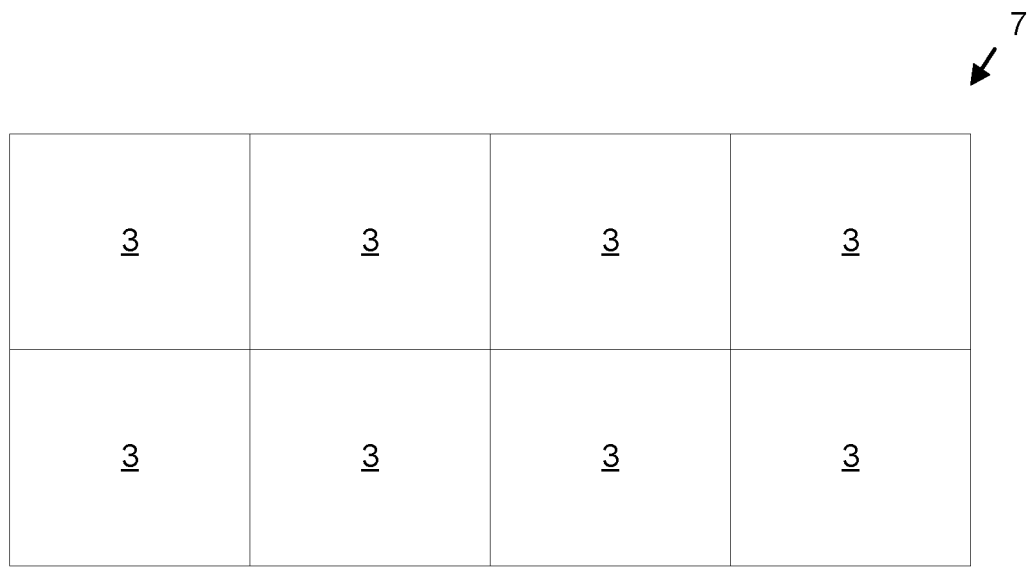
FIG. 2C is a schematic diagram illustrating one embodiment of frame regions.

FIG. 2C is a schematic diagram illustrating one embodiment of frame regions 3 in a removed frame 7 and/or an image frame 5. In the depicted embodiment, the removed frame 7 and/or an image frame 5 is divided into a rectangular grid of one or more regions 3. In this embodiment, all regions 3 have rectangular shapes and are equal in size. In one embodiment, a first frame region 3 covers a feature of the subject 110. Frame regions 3 of other shapes may be employed. In one embodiment, a frame region 3 only includes a single subject 110.

Figure 2D:
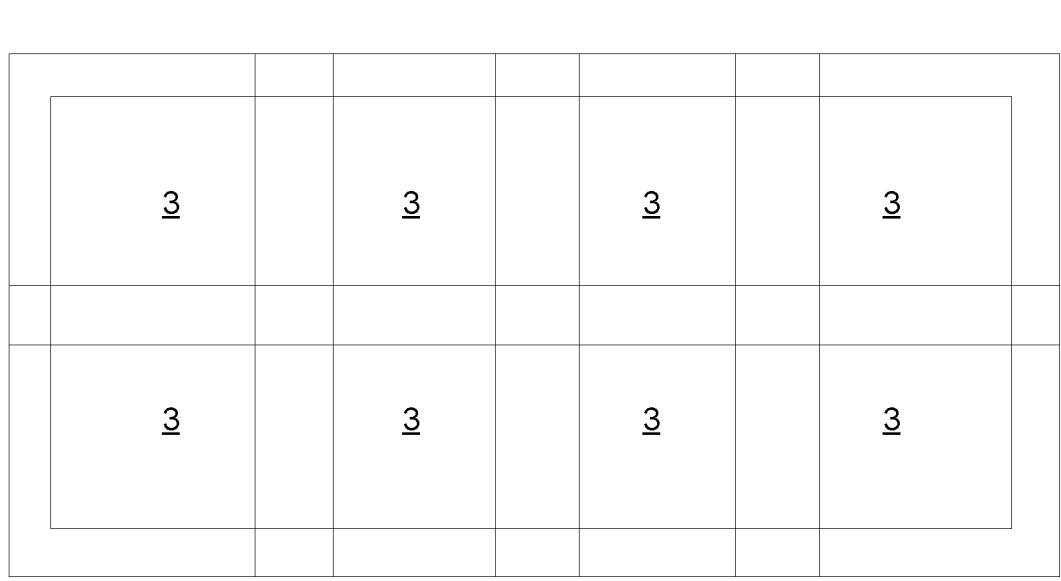
FIG. 2D is a schematic diagram illustrating one alternate embodiment of frame regions.

FIG. 2D is a schematic diagram illustrating one alternate embodiment of frame regions in a removed frame 7 and/or an image frame 5. In the depicted embodiment, the removed frame 7 and/or an image frame 5 is divided into a rectangular grid of one or more overlapping regions 3. In this embodiment, all regions 3 have rectangular shapes and are equal in size. In one embodiment, a first frame region 3 covers a feature of the subject 110.

FIG. 2E is a schematic block diagram illustrating one embodiment of the frame region 3. The frame region 3 is depicted as data organized in a data structure. The data structure may be stored in a memory. In the depicted embodiment, the frame region 3 includes a plurality of pixels 9 and corresponding pixel weights 11. In one embodiment, the frame region 3 further includes a region sum 277, a scaler time signal 271, a low order subspace decomposition 273 and/or a decomposition frequency 275. The region sum 277, scaler time signal 271, low order subspace decomposition 273, and/or decomposition frequency 275 may be calculated for the frame region 3 as will be described hereafter.

FIG. 2F is a schematic block diagram illustrating one embodiment of system data. In the depicted embodiment, the system data includes a logistic regression classifier 281, a breathing model 283, a crying model 285, a smiling model 287, a smiling image 289, a notification 291, a position model 293, a sleep model 295, a CPAP model 297, and the device database 2999. The logistic regression classifier 281 may be trained on video streams 120 of a plurality of subjects 110. The logistic regression classifier 281 is described hereafter in FIG. 2F.

The breathing model 283 may be trained to determine breathing. The crying model 285 may be trained to identify crying. The smiling model 287 may be trained to determine smiling.

The smiling image 289 may be an image of the subject 110 captured by the camera 105 in response to determining that the subject 110 is smiling. The smiling image 289 may be stored in a memory.

The notification 291 may comprise a message that is communicated to a user. The notification 291 may be communicated via the display 119, the speaker 121, and/or the mobile application 141. In one embodiment, a notification 291 is communicated in response to the base station 333 being out of communication range of the monitor device 123.

The position model 293 may be trained to determine a sleep position 341. The sleep model 295 may be trained to identify a sleep status 343. The CPAP model 297 may be trained to identify use of the CPAP machine and/or improper use of the CPAP machine. The device database 299 may store network addresses for the camera 105, the base station 133, and/or the electronic device 103.

Figure 2G:
FIG. 2G is a schematic block diagram illustrating one embodiment of a logistic regression classifier.

FIG. 2G is a schematic block diagram illustrating one embodiment of the logistic regression classifier 281. In the depicted embodiment, the logistic regression classifier 281 receives a D energy signal 311, an average of D[1] and D[2] energy signals 313, an average of D[3] and D[4] energy signals 315, a square root of a sum of the squares of Y[1] and Y[2] output signals 317, and a square root of a sum of the squares of Y[3] and Y[4] output signals 319. The logistic regression classifier 281 may generate a output probability 318 of the large-scale motion 267, the breathing event 265, and/or no motion.

Figure 2H:
FIG. 2H is a schematic block diagram illustrating one embodiment of a binary mask.

FIG. 2H is a schematic block diagram illustrating one embodiment of a binary mask 320. The binary mask 320 may be organized as a data structure in a memory. In the depicted embodiment, the binary mask 320 includes a mask value 321 for each of a plurality of pixels 9. In one embodiment, the mask value 321 is a binary value that indicates whether the corresponding pixel 9 will be considered in calculations. In an alternate embodiment, the mask value 321 is a scaler value that indicates the degree to which the corresponding pixel 9 will be considered in calculations.

Figure 2I:
FIG. 2I is a schematic block diagram illustrating one embodiment of a skin mask and a skin histogram.

FIG. 2I is a schematic block diagram illustrating one embodiment of a skin mask 325 and a skin histogram 326. The skin mask 325 maybe organized as a data structure in a memory. In the depicted embodiment, the skin mask 325 includes a color value 327 for each of a plurality of pixels 9. In one embodiment, a probability transform 329 is associated with each color value 327. The probability transform 329 may indicate the probability that the color value 327 corresponds to skin of the subject 110 at the pixel 9.

The skin histogram 326 may be organized as a data structure in a memory. In one embodiment, the skin histogram 326 records the number of pixels 9 that have a given color value 327 and/or range of color values 327. In a certain embodiment, the skin histogram 326 records the number of pixels 9 that have a given probability transform 329 and/or range of probability transforms 329.

Figures 2J, 2K:
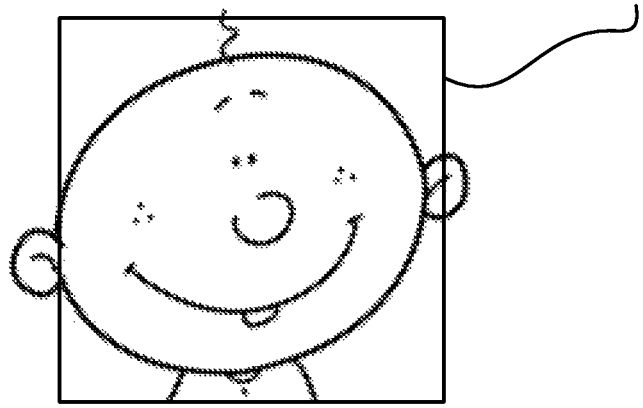
FIG. 2J is a schematic block diagram illustrating one embodiment of a kernel matrix and background signal.
FIG. 2K is a drawing illustrating one embodiment of a face region.

FIG. 2J is a schematic block diagram illustrating one embodiment of a kernel matrix 330 and background signal 333. The kernel matrix 330 may be organized as a data structure in a memory. The kernel matrix 330 may be calculated from sampled points of the video stream 120 with a variable variance. A mean vector 331 may be generated from the kernel matrix 330. In one embodiment, the background signal 333 is the mean vector 331. In one embodiment, a background signal filter 335 removes the background signal 333 from the image frame 5 and/or removed frame 7 using the kernel matrix 330, the mean vector 331, and/or background signal 333. FIG. 2K is a drawing illustrating one embodiment of a face region 337. The face region 337 may bound a face of the subject 1110. The face region 337 may be square. Alternatively, the face region may be rectangular, circular, and/or trapezoidal.

Figure 3A:
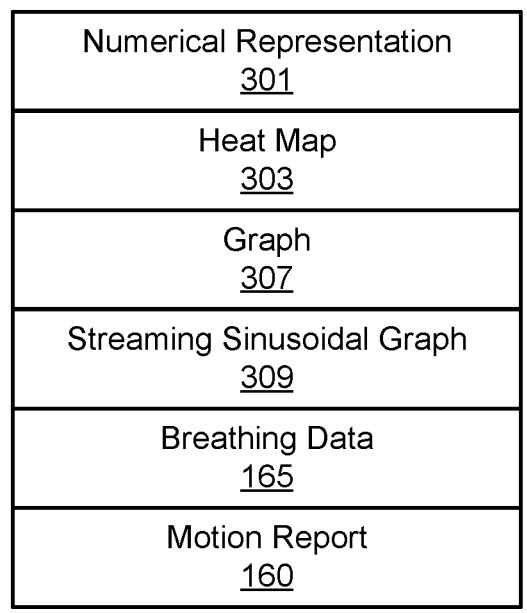
FIG. 3A is a schematic block diagram illustrating one embodiment of breathing data.

FIG. 3A is a schematic block diagram illustrating one embodiment of a breathing report 300. The breathing report 300 may be organized as a data structure that is communicated via the display 119, the speaker 121, and/or the mobile application 141. The breathing report 300 may include a numerical representation 301, a heat map 303, a graph 307, and/or a streaming sinusoidal graph 309. In addition, the breathing report 300 may include the breathing data 165 and/or the motion report 160.

The numerical representation 301, the heat map 303, the graph 307, and/or the streaming sinusoidal graph 309 may each singly and/or in combination communicate the breath rate 231, the maximum inter-breath interval 233, the minimum inter-breath interval 235, the inter-breath interval statistics 237, the inter-breath interval histogram 239, the motion frequency 243, the motion magnitude 245, the motion duration 247, the sleep length 249, the sleep quality 251, the sleep intervals 253, the sleep position 341, the sleep status 343, and/or the apnea event data 241.

Figure 3B:
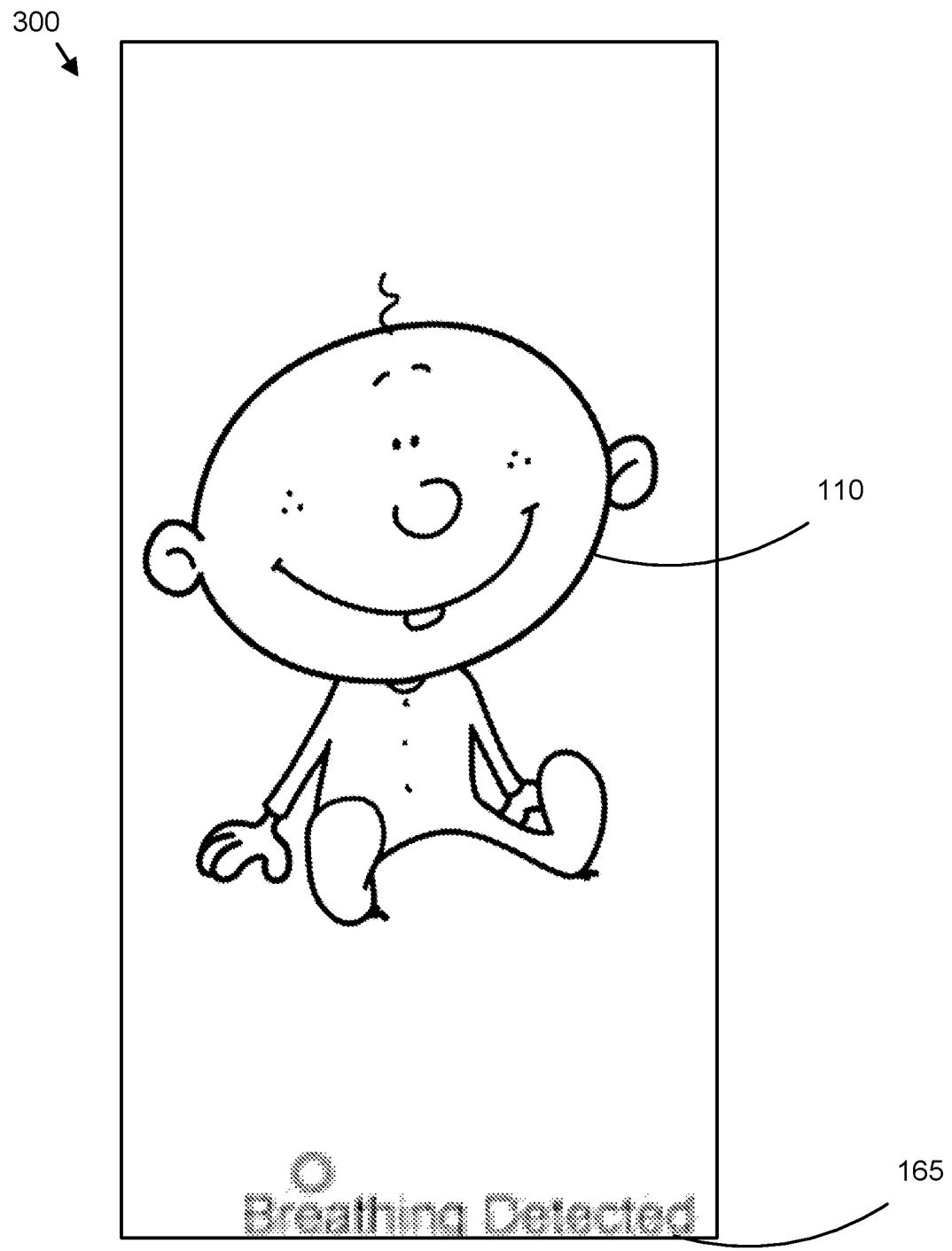
FIG. 3B is a drawing illustrating one embodiment of a breathing report.

FIG. 3B is a drawing illustrating one embodiment of a breathing report 300. In the depicted embodiment, the breathing report 300 presents a full image of the subject 110 and breathing data 165 on the mobile application 141. The breathing data 165 may summarize that breathing is detected.

Figure 3C:
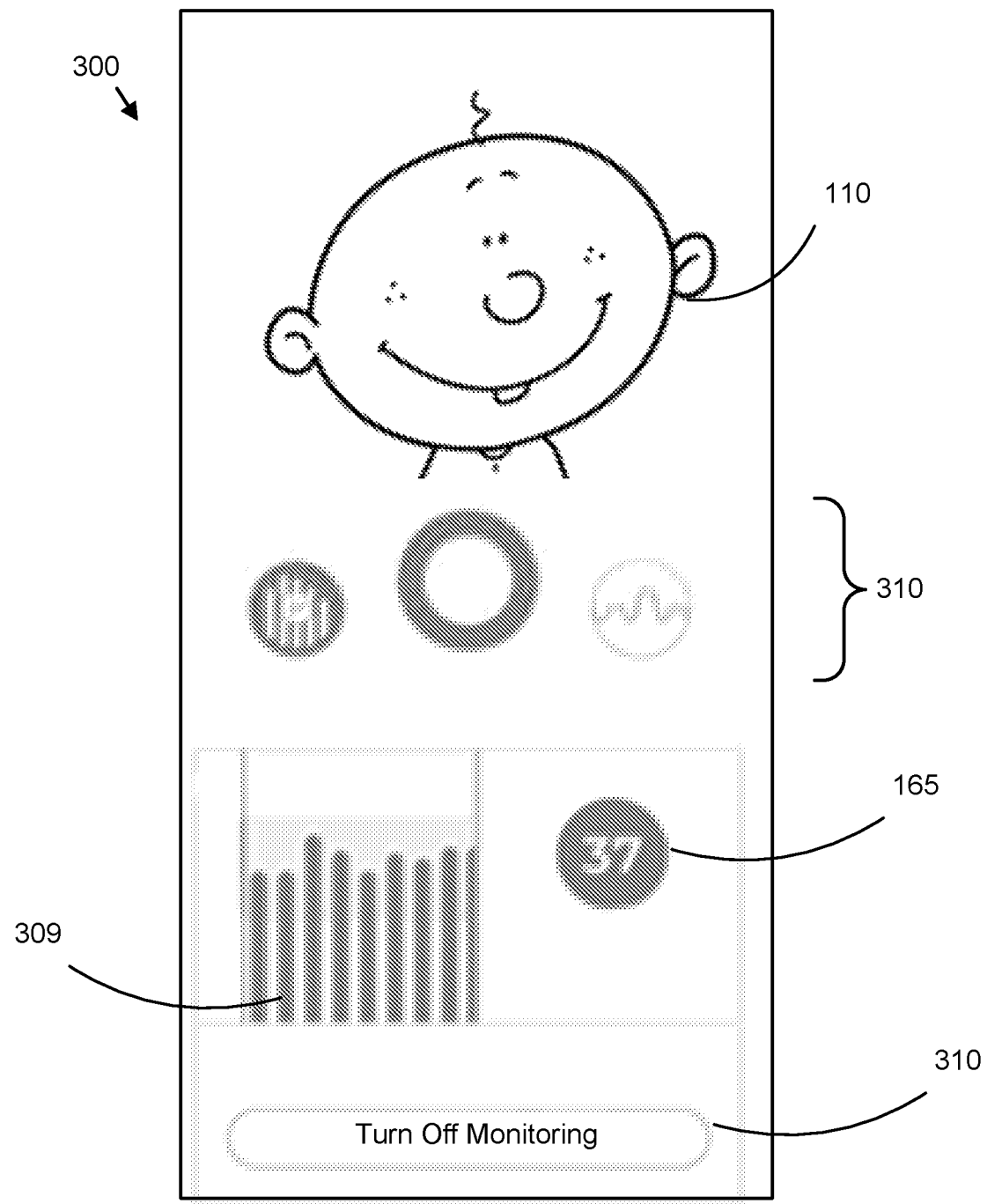
FIG. 3C is a drawing illustrating one alternate embodiment of a breathing report.

FIG. 3C is a drawing illustrating one alternate embodiment of a breathing report 300. In the depicted embodiment, the breathing report 300 presents a partial image of the subject 110, a graph 309, breathing data 165, and controls 310.

Figure 3D:
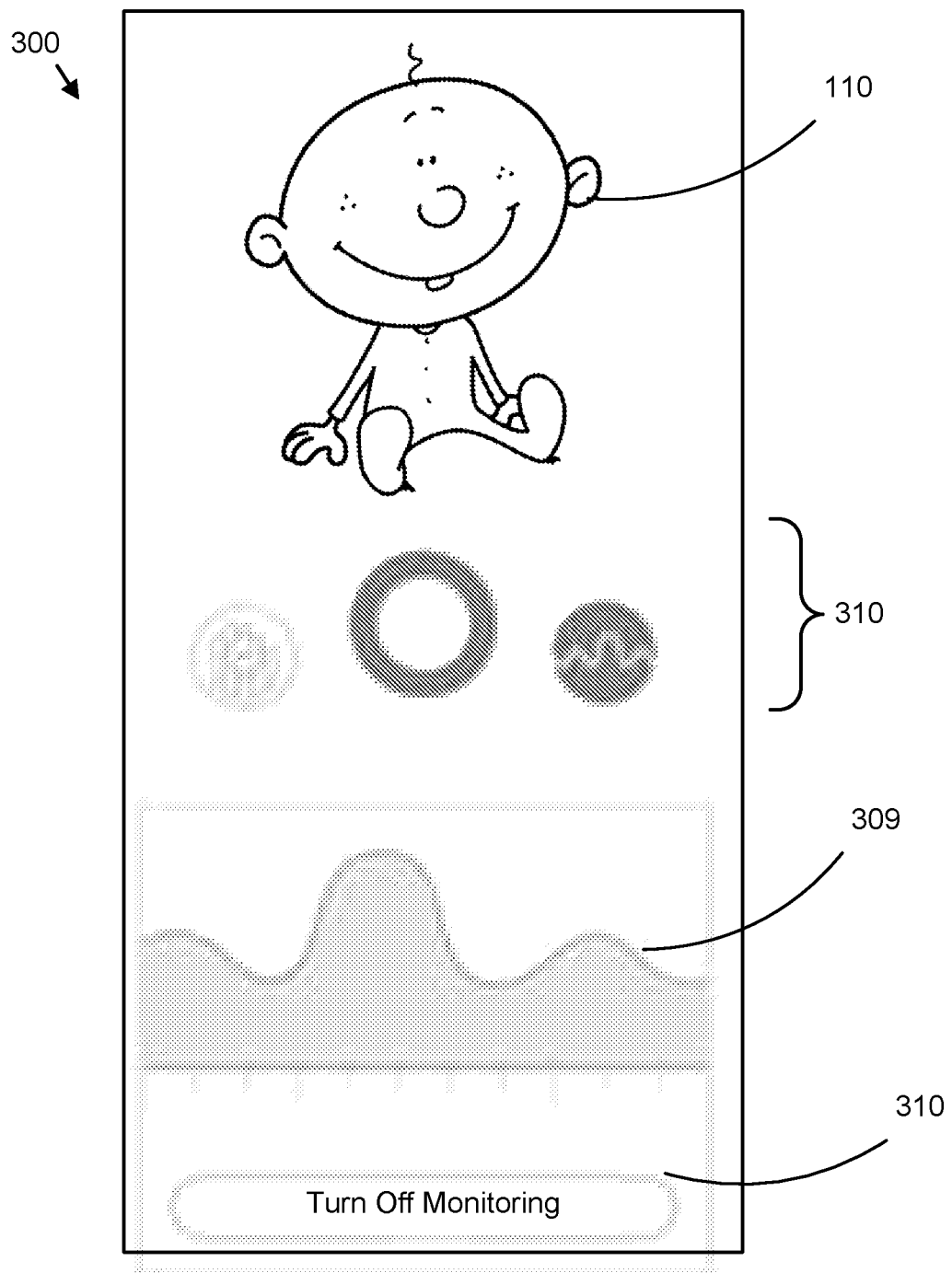
FIG. 3D is a drawing illustrating one alternate embodiment of a breathing report.

FIG. 3D is a drawing illustrating one alternate embodiment of a breathing report 300. In the depicted embodiment, the breathing report 300 presents the a full image of the subject 110, a graph 309, and controls 310.

Figure 3E:
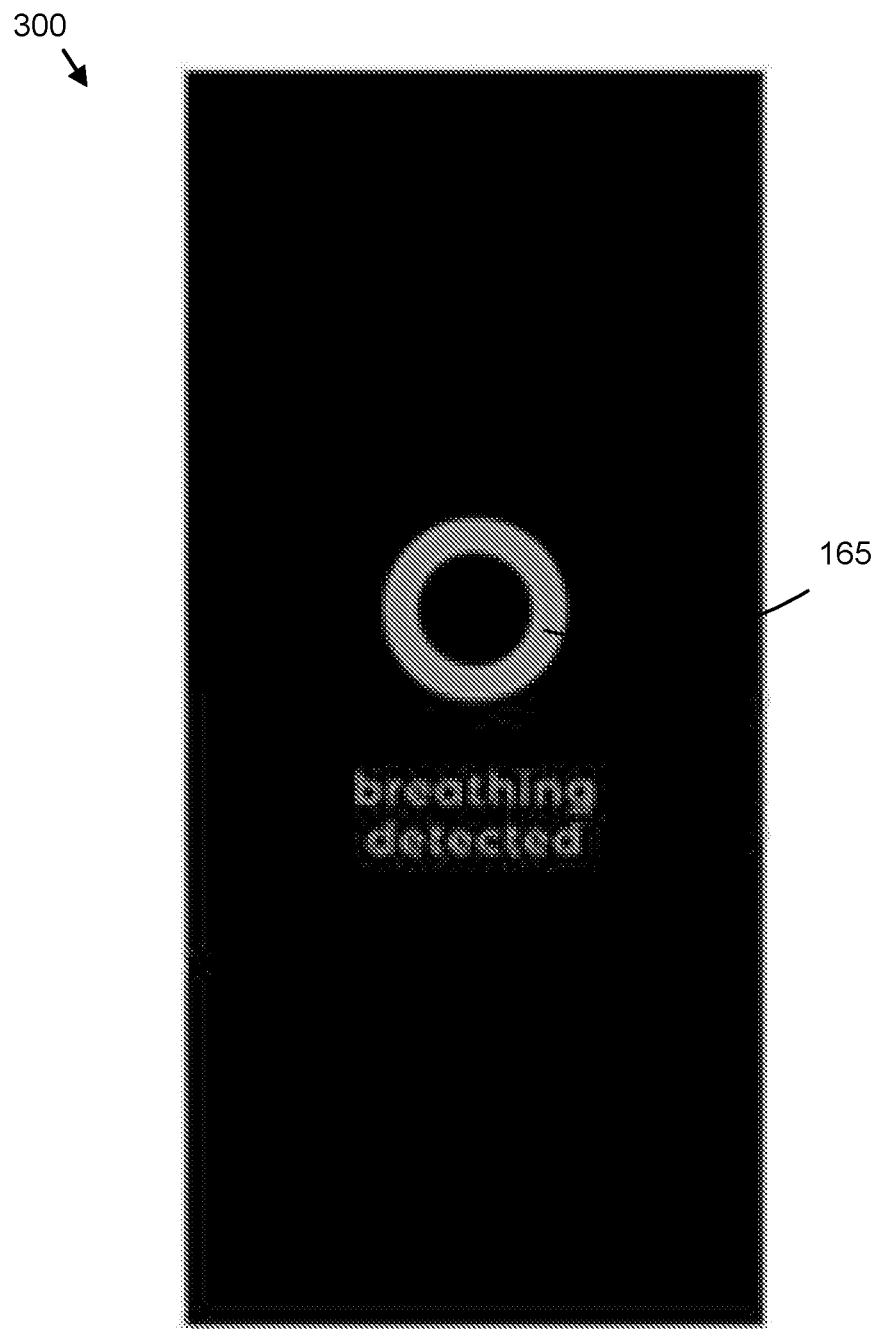
FIG. 3E is a drawing illustrating one alternate embodiment of a nightstand mode breathing report.

FIG. 3E is a drawing illustrating one alternate embodiment of a nightstand mode breathing report 300. In the depicted embodiment, the breathing data 165 is presented in dark mode.

Figure 4A:
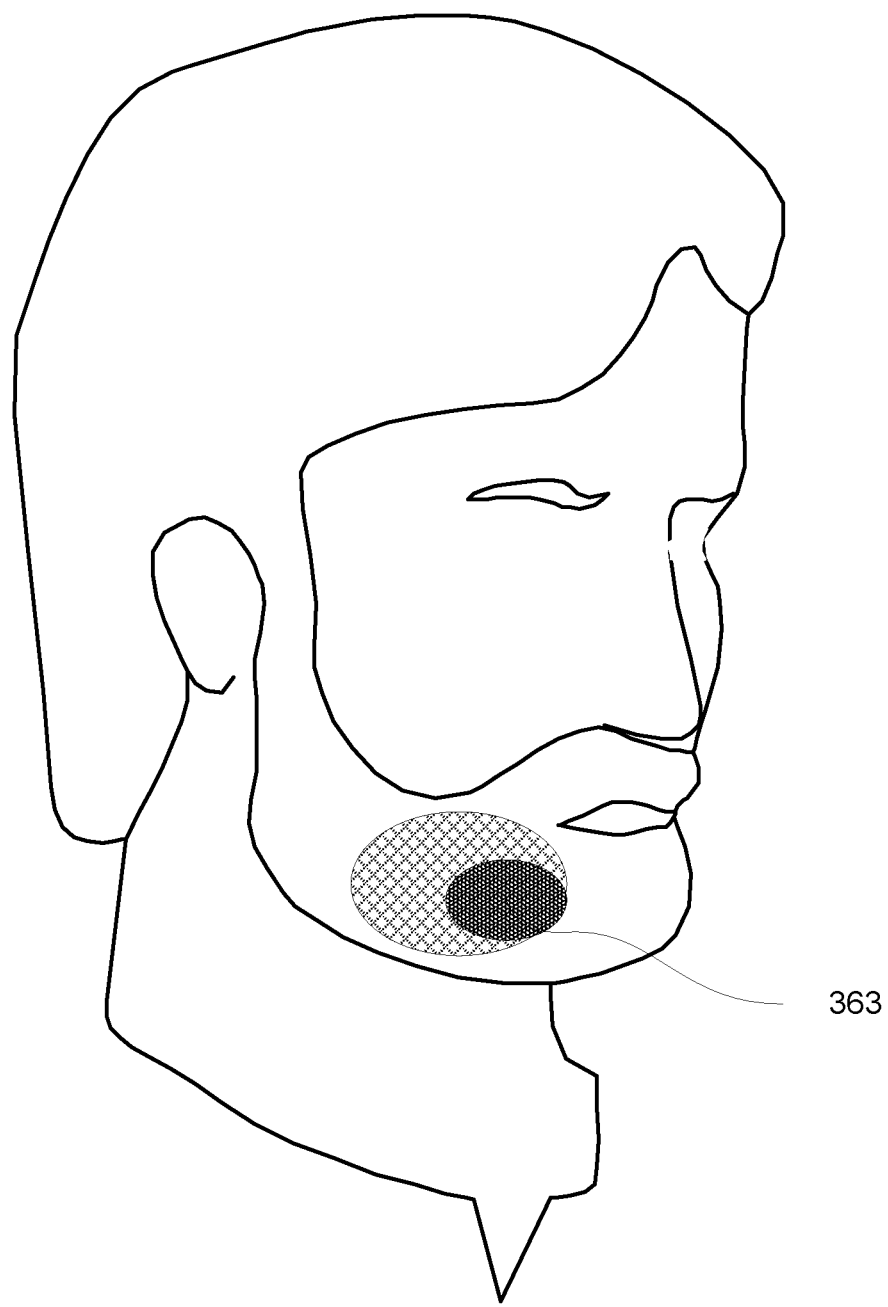
FIG. 4A is a drawing illustrating one embodiment of a heat map.

FIG. 4A is a drawing illustrating one embodiment of a heat map 363. In the depicted embodiment, a video stream 120 of the subject 110 is shown with the heat map 363 superimposed on the video stream 120. In one embodiment, the breath rate 231 from a plurality of breathing events 265 is encoded as the heat map 363. The heat map 363 may be overlaid on the video stream 120 for display to a user.

Figure 4B:
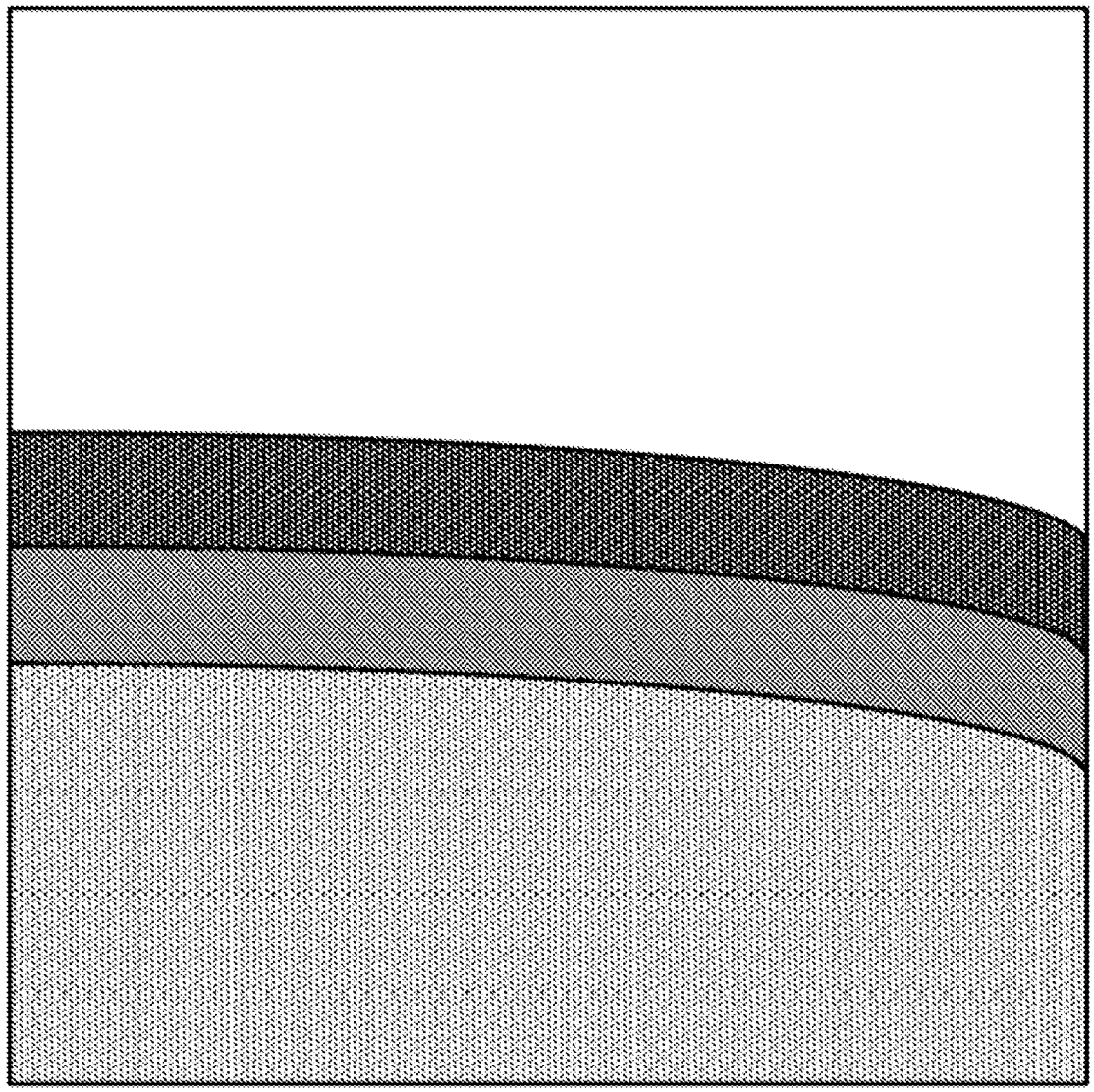
FIG. 4B is a drawing illustrating one alternate embodiment of a heat map.

FIG. 4B is a drawing illustrating one alternate embodiment of a heat map 363. In the depicted embodiment, a video stream 120 of the subject 110 such as the chest region of the subject 110 is shown with a heat map 363 superimposed on the video stream 120. The heat map 363 may be encoded with the large-scale motion 267 of the subject 110. In one embodiment, the heat map 363 encodes the motion magnitude 245 of the subject 110.

Figure 4C:
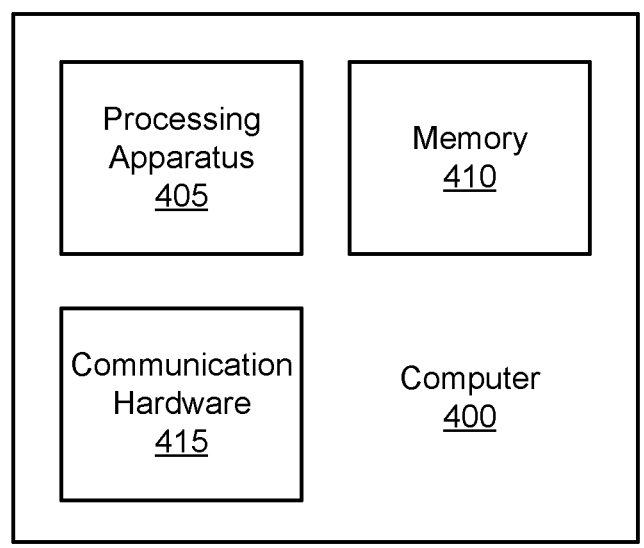
FIG. 4C is a schematic block diagram illustrating one embodiment of a computer.

FIG. 4C is a schematic block diagram illustrating one embodiment of the computer 400. The computer 400 may be embodied in the hardware modules 115. In the depicted embodiment, the computer includes a processing apparatus 405, a memory 410, and communication hardware 415. The memory 410 may include a semiconductor storage device. The memory 410 may store code. The processing apparatus 405 may execute the code. The communication hardware 415 may communicate with other elements of the monitor device 123, the base station 133, and/or the network 116.

Figure 4D:
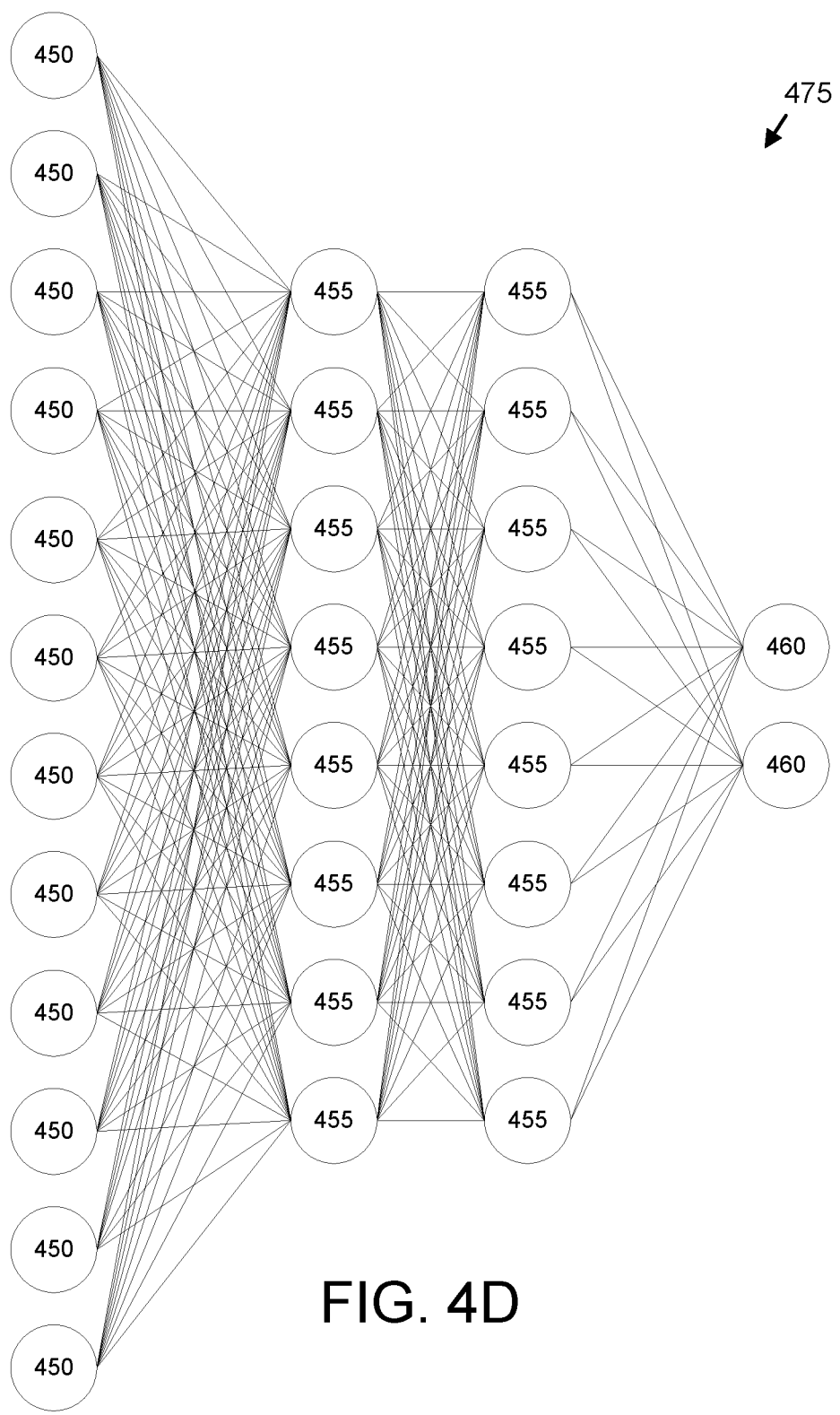
FIG. 4D is a schematic diagram illustrating one embodiment of a neural network.

FIG. 4D is a schematic block diagram illustrating one embodiment of a neural network 475. In the depicted embodiment, the neural network 475 includes one or more hidden neurons 455. The hidden neurons 455 receive inputs from one or more input neurons 450 and communicate with one or more output neurons 460. The output neurons 460 may indicate predictions such as breathing normally and/or moving. The neural network 475 may be trained with data as the breathing model 283, the crying model 285, the smiling model 287, the position model 293, the sleep model 295, and/or the CPAP model. In addition, data may be presented to the input neurons 450 of the trained neural network 475 and the output neurons 460 may predictions such as the breathing signal 183.

Figure 5A:
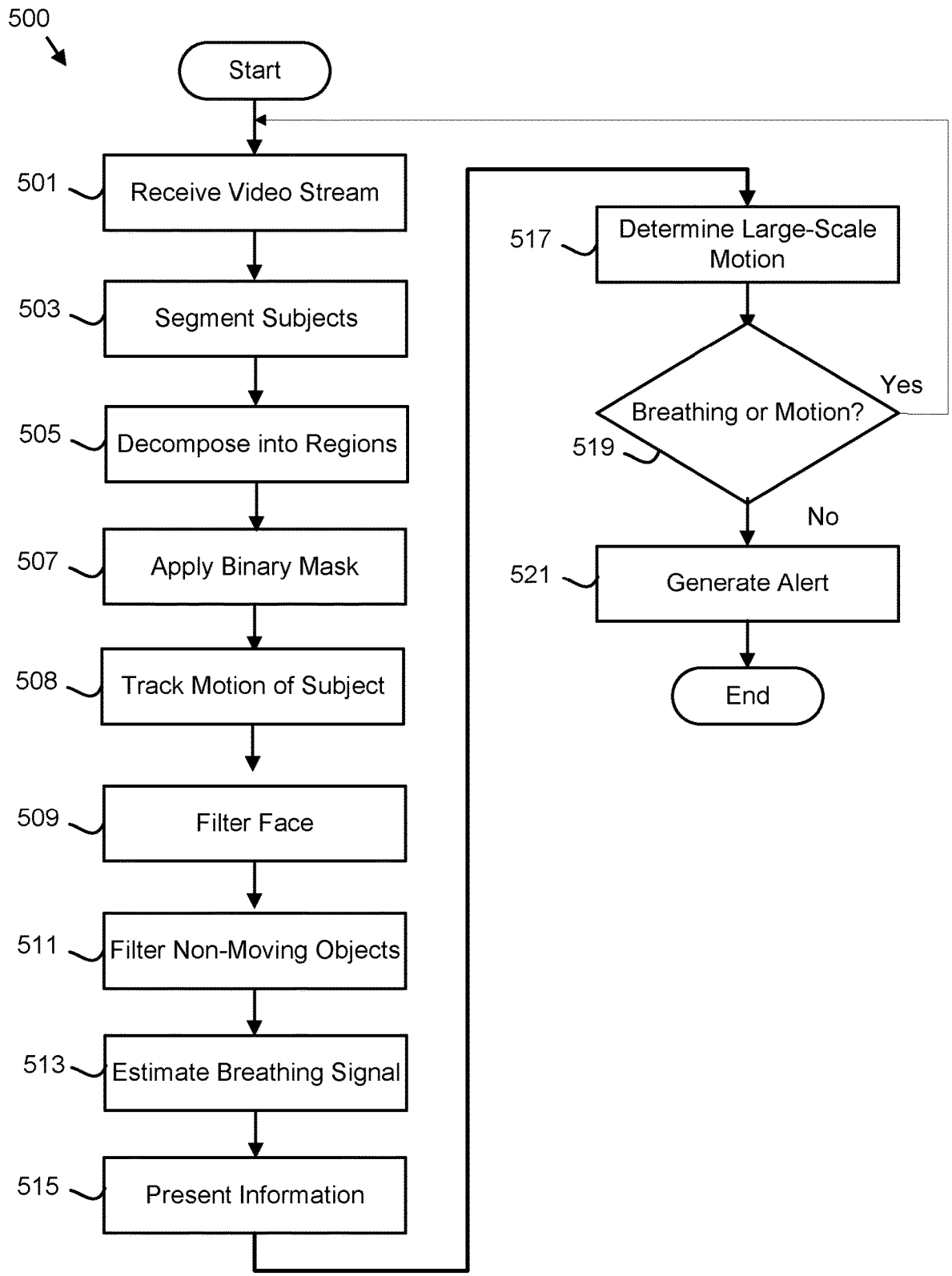
FIG. 5A is a schematic flow chart diagram illustrating one embodiment of an alert generation method.

FIG. 5A is a schematic flow chart diagram illustrating one embodiment of an alert generation method 501. The method 500 may estimate the breeding signal 183 and generate an alert if no breathing or motion is detected. The method 500 may be performed by the system 100 and/or processing apparatus 405.

The method 500 starts, and in one embodiment, the processing apparatus 405 receives 501 the video stream 120 of the subject 110. The video stream 120 may comprise Red Green Blue (RGB) image frames 5, Cyan, Magenta, Yellow, and Black (CMYK) image frames 5, or grayscale image frames 5. In one embodiment, static pixels are removed to form the removed frame 7 as will be described hereafter.

The processing apparatus 405 may segment 503 a first subject 110 of a plurality of subjects 110 from the video stream 110. The large-scale motion 267 and/or the breathing signal 183 may be determined for the first subject 110 and/or each subject 110 in each segment.

The processing apparatus 405 may decompose 505 each image frame 5 into a plurality of frame regions 3. A first frame region 3 may cover a feature of the subject 110. The image frame 5 and/or removed frame 7 is decomposed into frame regions 3 for further processing. A frame region 3 is a set of pixels in the original image frame 5 and/or removed frame 7. Typically, the frame regions 3 are rectangular subsets of pixels for convenience, such as shown in FIG. 2C. The frame regions 3 may be laid out in a rectangular grid. Frame regions 3 may be laid out in a manner such that the frame regions 3 overlap with their nearest neighbor frame regions 3 as shown in FIG. 2D. The number of frame regions 3 is not proscribed. A single frame region 3 could encompass the whole of the original frame image 5. At the other extreme is letting each pixel be its own frame region 3. The guiding principle in choosing the number of frame regions 3 is choosing the size to cover a single physical feature on the subject 110 being monitored. A physical feature could be the head, neck, shoulder, chest, tummy, and so on. The overlap pattern is chosen to provide adequate coverage of the physical features. For example, a 50% overlapping pattern allows the coverage of the physical features to be independent of the placement of the camera 105 and the subject 110 in the field of view.

The processing apparatus 405 may apply 507 a binary mask to image frames 5 and/or removed frames 7. The generation and application of the binary mask is described in more detail in FIG. 5D.

The processing apparatus 405 may track 508 motion of the subject 110. The motion may be tracked 508 using the motion detector 127. In addition, the motion may be tracked 508 from the video stream 120. The motion of the subject 110 may be tracked with a Gaussian filter coupled to a Hanning window. In one embodiment, the processing apparatus 405 filters the motion of the subject 110 from the video stream 120. In one embodiment, the motion of the subject 110 is tracked 508 as described in FIG. 6F.

The processing apparatus 405 may further filter 509 a face of the subject 110 in the image frames 5 and/or removed frames 7 so that only the face remains. In one embodiment, the face is identified from the skin histogram 326 as a most common color value 327. The generation of the skin histogram 326 is described in more detail in FIG. 5E.

Figure 5B:
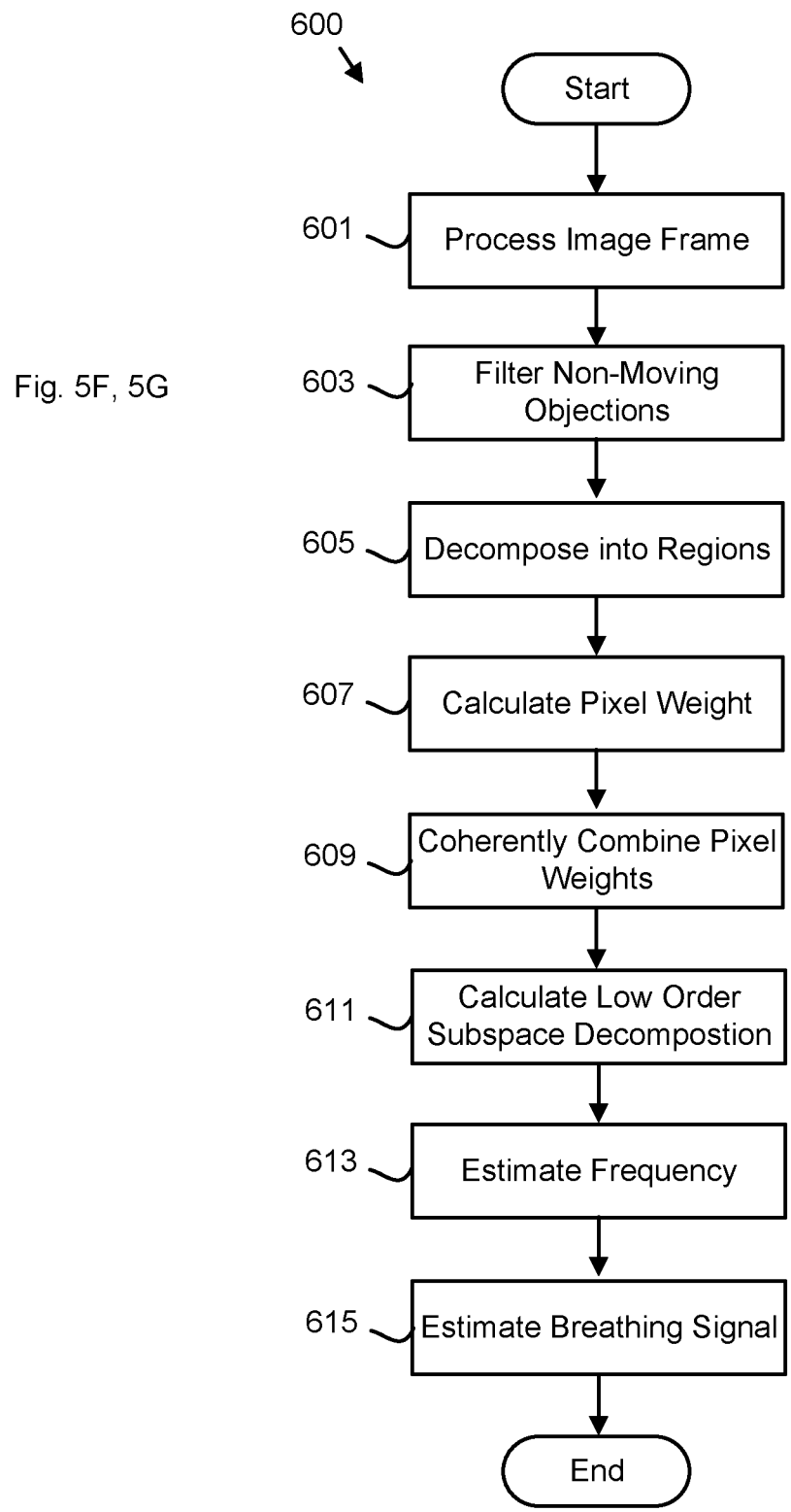
FIG. 5B is a schematic flow chart diagram illustrating one embodiment of a breathing signal estimation method.

The processing apparatus 405 may further filter 511 nonmoving objects 151 from the image frames 5. In one embodiment, the background signal 333 is filtered 511 from the image frames 5 using the background signal filter 335. In addition, the sparse matrix S 130 may be calculated to represent the moving objects 150. FIGS. 5B, 5F, and 5G describe filtering embodiments in more detail.

The processing apparatus 405 may estimate 513 the breathing signal 183 from the video stream 110, the image frames 5, and/or the removed frames 7. The breathing signal 183 may be estimated 513 by applying a Hilbert transform to the removed frames 7.

In a certain embodiment, the breeding signal 183 is estimated 513 from a compressed video stream 120 that is compressed with a video compression algorithm. The video compression algorithm performs motion estimation as a sub-step in the video compression and generates motion estimation products. The motion estimation products may be the moving objects 150 used to detect the small motions of the breathing signal 183. In one embodiment, the video compression algorithms are not changed. Instead the motion estimation products already computed in the process of video compression are the moving objects 150 used to detect the breathing signal 183.

Figure 5C:
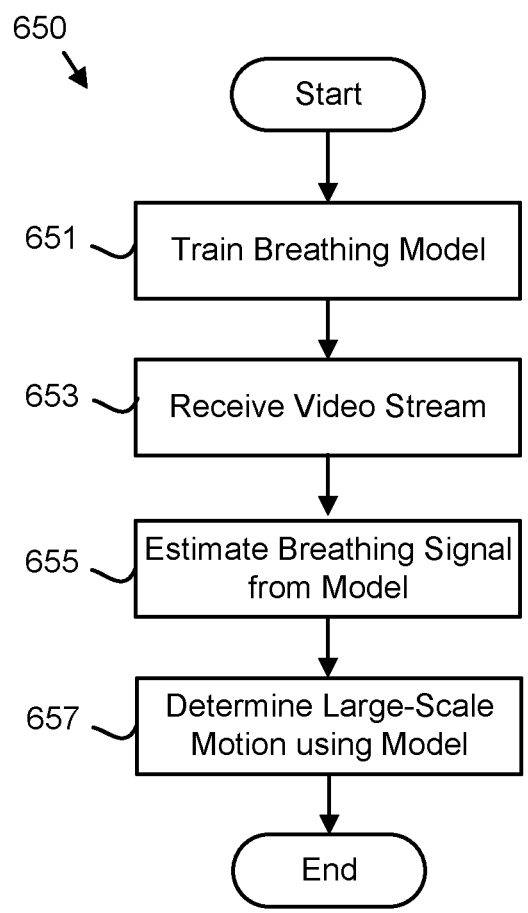
FIG. 5C is a schematic flow chart diagram illustrating one alternate embodiment of a breathing signal estimation method.

Embodiments of the estimation 513 of the breathing signal 183 are described in more detail in FIGS. 5B and 5C. A breathing event 265 may be determined if there is a periodic breathing signal 183.

The processing apparatus 405 may present 515 information. The information may comprise the video stream 120, the breathing report 300, and/or the audio stream 131. The information may be presented 515 via the mobile application 141. In addition, the information may be presented via the display 119 and/or speaker 121. In one embodiment, the user selects the format of the information. In addition, the user may mute the audio signal 131.

The processing apparatus 405 may determine 517 the large-scale motion 267 from the breathing signal 183. In addition, the large-scale motion 267 may be determined 517 from moving objects 150 remaining in the removed frames 7. If there are moving objects 150, then the large-scale motion 267 occurred.

The processing apparatus 405 determines 519 whether one of the large-scale motion 267 and/or the breathing event 265 occurred. If the large-scale motion 267 and/or breathing event 265 is determined 519, the processing apparatus 405 continues to receive 501 the video stream 120. If no large-scale motion 267 and no breathing event 265 is determined 519, the processing apparatus 405 generates 521 an alert and the method 500 ends. The alert may be generated 521 by communicating a notification 291 via the mobile application 141. In addition, the alert may be generated 521 by communicating a notification 291 via the speaker 121 and/or display 119.

FIG. 5B is a schematic flow chart diagram illustrating one embodiment of a breathing signal estimation method 600. The method 600 may estimate the breathing signal 183. The method 600 may be performed by the system 100 and/or processing apparatus 405.

The method 600 starts, and the processing apparatus 405 processes 601 each image frame 5. The processing apparatus 405 may convert the RGB or CMYK image frames 5 to grayscale. The image frames 5 may be formatted from integers such as 8-bit integers to floating point values.

In one embodiment, the image frame 5 is 720×1280 pixels. These image frames 5 are received at the frame rate. In one embodiment, the frame rate is 20 frames/second. The image frames 5 may be resized. In one embodiment, the image frame 5 is down-sampled by a factor of four yielding a 180×320 pixel image. The input image size and resizing impact much of the downstream processing complexity. Cameras 105 typically use video compression, which reduces the number of bits that must be transported to memory 410 on the processing apparatus 405 over a bus such as USB or PCIe. Camera settings may be used to configure the video quality and compression. In one embodiment, the compression is MP4 and the configuration sets key frames to occur once every 18 seconds or 360 frames at 20 frames/second.

The processing apparatus 405 may remove 603 the non-moving objects 151 from each image frame 5 to yield the removed image 7. In one embodiment, the mean vector 331 in each pixel of the image frame 5 may be estimated and removed yielding a mean removed image 7. In a certain embodiment, mean removal is done using an averaging filter. In another embodiment, the mean is estimated and removed using a Kalman filter. In this case, a scalar Kalman filter is used. A different Kalman filter is applied in each pixel in the image frame 5. The exemplary steps in a scalar Kalman filter for mean removal are listed below as Equation 1 for pixels 9 of the matrix X 125, matrix S 130, and matrix L 135. These steps are repeated each time a new image is received.

Equation 1

(a) Adjust process noise covariance for key frames.
If(n == 359)
Q = 1.0
n = 0
else Q = 0.1
n = n + 1
end
(b) K = Pm/(Pm + R)
(c) Tmp2 = K*K
(d) Tmp1 = 1 + Tmp2 − 2*K
(e) Pp = Tmp1*Pm + Tmp2*R
(f) Pm = Pp + Q
Steps (a) through (f) are updated once for each image. These parameters are the same for every pixel in the image. Repeat the following steps for each pixel in the image
(g) e[i] = data[i] − x[i] (compute the apriori error)
(h) x[i] = x[i] + K*e[i] (update the estimated mean)
(i) y[i] = data[i] − x[i] (compute the aposteriori error)

In these steps, y[i] is the grayscale value in the i-th pixel. This whole process is initialized prior to processing the first image by: R=0.5, Q=1.0, Pm=1.0, n=0. The Kalman filter is used in the preferred embodiment because it provides a principled way to adaptively adjust the process noise covariance whenever a key frame is encountered. Increased noise variance is used to allow the mean to track to a new level quickly after the key frame is encountered.

The processing apparatus 405 may decompose 605 each removed image 7 into a plurality of frame regions 3 as described in FIG. 5A. A first removed frame 7 may cover a feature of the subject 110. The removed image 7 is decomposed into frame regions 3 for further processing. A frame region 3 is a set of pixels in the removed frame 7. Typically, the frame regions 3 are rectangular subsets of pixels for convenience, such as shown in FIG. 2C. The frame regions 3 may be laid out in a rectangular grid. Frame regions 3 may be laid out in a manner such that the frame regions 3 overlap with their nearest neighbor frame regions 3 as shown in FIG. 2D.

In one embodiment the frame image 5 is 180×320 pixels and the frame regions 3 are 30×40 pixel regions with 50% overlap. This yields a 11×15 grid of frame regions 3. In this example, there are 165 frame regions 3 total.

Much of the subsequent processing is performed independently in each frame region 3. This is done because breathing is a highly localized physical phenomenon. Breathing may affect the head, neck, shoulders, chest, belly, etc. These physical objects may occupy only a small fraction of the total frame image 5 and/or removed image 7. Observing small motions of these physical features due to breathing is more likely in the frame regions 3 than in the whole image because small movements of a physical feature may represent a larger fraction of a well-sized frame region 3 but would be only a small fraction in the whole frame image 5 and/or removed image 7.

In one embodiment, the processing apparatus 405 calculates 607 the pixel weight 11 for each pixel 9 of each frame region 3. Each pixel weight 11 may be one of a positive weight or a negative scalar. In one embodiment, each pixel 9 is weighted with a positive or negative scale pixel weight 11 so that information systematically accumulates across the whole frame region 3 as the region sum 277. Instead of destructively interfering, all pixels 9 are coherently combined leading to the largest possible weighted region sum 277. The process is adaptive in that it responds to changes in the video stream 120.

The processing apparatus 405 may further coherently combine 609 the pixel weights 11 for each frame region 3 as a time series of region sums 277 and/or a scalar time signal 271 for each frame region 3. The result of coherent spatial combining is a scalar valued region sum 277 in each frame region 3. When these region sums 277 are viewed over time, the region sums 277 are the signals that encode information about the activity states of interest: motion, breathing, and/or lifelessness. If the physical feature viewed in a frame region 3 is involved in breathing activity, then the region sum 277 will oscillate at the breath rate 231 as the scalar time signal 271 and/or breathing signal 183.

The pixel weights 11 are used to coherently combine the image pixels 9 in a manner that is equivalent to beamforming. In addition, the pixel weights 11 may be coherently combined 609 using adaptive beamforming. In one embodiment, the pixel weights 11 are coherently combined 609 using subspace tracking. The steps in the subspace tracking algorithm listed below in Equation 2 may be employed.

Equation 2

$Y=<W,X>$ (compute the inner product of the weight vector with the pixels in the region)      (a)

$D$=average value of $Y*Y$ (compute the average value of the energy in $Y$)      (b)

$S=Y/(D+\text{epsilon})$ (compute scale factor)      (c)

$E=X-W*Y$ (compute the error in a one-dimensional subspace representation)      (d)

$W=W+E*s$ (update the weight vector)      (e)

The variable Y is the region sum 277. It is the output of this processing stage. The weight array W is initialized to small random values. The value of epsilon is set to avoid dividing by zero. D is the average value of the energy in the region sum 277. This average value may be computed in many different ways. In one embodiment, the average value D uses a 61-point moving average. The subspace tracking algorithm of Equation 2 adapts W to be an orthonormal basis for the one-dimensional subspace in which the input region images X lie. It adapts to the fluctuations in the frame image 5 and/or removed image 7 and maximizes the energy D in the region sum Y 277. Thus, the inner product between W and X coherently combines the pixels in the region X. As a result, the spatial coherent combining 609 extracts the scalar time signal 271 as a scalar-valued time signal s[n] in each frame region 3.

The processing apparatus 405 may calculate 611 a low order subspace decomposition 273 of the scalar time signal 271 for each frame region 3. In one embodiment, the processing apparatus 405 calculates 611 the low order subspace decomposition 273 of the scalar time signal 271 for each frame region 3 to detect a quasi-periodic sinusoidal-like signal. Each real sinusoidal signal present as a component in the Four series explanation of the signal s[n] requires a two-dimensional subspace to explain it.

The low order subspace decomposition 273 is calculated 611 using a series of vectors S[n]=[s[n], s[n−1], s[n−2], . . . s[n−N+1]] where N is a parameter. In one embodiment, N=60 frames which corresponds to 3 seconds of video at 20 frames/second.

The low order subspace decomposition 273 of the scalar time signal 271 may perform updates as new data examples arrive from the camera 105 with low computational complexity, improving the efficiency of the processing apparatus 405. The algorithm of Equation 3 may calculate 611 the low order subspace decomposition 273. The inputs to this algorithm may be the 60×1 signal vectors S[n]. The internal variables are a collection of 60×1 weight vectors W[i], scalar projected signals Y[i], and energy signals D[i]. The dimension of the tracked subspace is a parameter. In one exemplary embodiment, a four-dimensional subspace is extracted. When the algorithm of Equation 3 is used to extract a low-order orthonormal basis, the following steps are used. The steps extract a four-dimensional subspace, but may be employed for other dimensions based in the value of i.

Equation 3

$X[1]=S[n]$      Initialize:

For $i$=1,2,3,4

$Y[i]=<W[i],X[i]>$ (compute scalar projected signal to be the inner product of $W[i]$ and $X[i]$)      (a)

$D[i]$=average of $Y[i]*Y[i]$ (update average energy in $Y[i]$)      (b)

$T=Y[i]/(D[i]+1)$ (compute the scale factor)      (c)

$E[i]=X[i]-W[i]*Y[i]$ (compute the apriori error between $X[i]$ and it's projection onto $W[i]$)      (d)

$W[i]=W[i]+T*E[i]$ (update weights/basis function)      (e)

$X[i+1]=X[i]-W[i]*Y[i]$ (compute the aposteriori error)      (f)

The processing apparatus 405 estimates 613 a decomposition frequency 275 of the low order subspace decomposition 273 for each frame region 3 as the breathing signal 183. When a sinusoidal breathing signal 183 is present, the first two basis functions W[1] and W[2] of Equation 3 resemble sine and cosine functions at the breath rate 231. The breath rate 231 may be found by estimating the frequency in the vectors W[1] and W[2].

In one embodiment, the breath rate 231 is calculated using Equation 4 as follows:

Consider the elements of W[1] and W[2] as the real and imaginary parts of a complex-waveform. Compute the phase of this waveform by Phi[i]=atan 2(W[2][i], W[1][i]), where atan 2 is a four-quadrant inverse tangent function such as is found in most numerical packages and libraries, and W[1][i] and W[2][i] are the i-th elements of the vectors W[1] and W[2], where i=1, 2, 3, . . . , 60.

The atan 2 function returns phases in the range −pi<=Phi[i]<pi. The phase may be unwrapped by detecting and correcting phase jumps by more than pi radians. Phase unwrapping is a commonly used signal processing operation and will be appreciated by one with ordinary skill in the art.

The instantaneous frequency is defined to be the slope of the phase. The phase slope is estimated by fitting a line to the unwrapped phase. Line fitting is a well-known problem. One embodiment uses linear least squares to fit a line to the phase function. The parameters of line are the slope and intercept. After the line fit is performed, the slope is obtained. The decomposition frequency 275 may be the slope of the estimated line. Some scale factors may be applied to obtain the decomposition frequency 275 with appropriate units. The decomposition frequency 275 may also equal to the breath rate 231. Therefore, the decomposition frequency 275 may be expressed in units of breaths/minute.

The quality of the line fit may be evaluated using the sum of squared residuals (SSR). Residuals are computed by subtracting the estimated line from the unwrapped phase Phi[i]. The sum of squares of these residuals is the SSR.

The processing apparatus 405 may estimate 615 the breathing signal 183 from the decomposition frequency 257 and the method 600 ends. The breathing signal 183 may be the decomposition frequency 257. In one embodiment, the breathing signal 183 is the filtered decomposition frequency 257.

The breathing signal 183 may be estimated 615 using the logistic regression classifier 281. In one embodiment, the logistic regression classifier 281 receives a feature vector comprising the D energy signal 311 from the low order subspace decomposition, the average of D[1] and D[2] energy signals 313 from the low order subspace decomposition, the average of D[3] and D[4] energy signals 315 from the low order subspace decomposition, the square root of a sum of the squares of Y[1] and Y[2] output signals 317 from the low order subspace decomposition, and/or the square root of a sum of the squares of Y[3] and Y[4] output signals 319 from the low order subspace decomposition and generates an output probability 318 of the large-scale motion 267, the breathing event 265, and/or no motion.

FIG. 5C is a schematic flow chart diagram illustrating one alternate embodiment of a breathing signal estimation method 650. The method 650 estimates the breathing signal 183 and determines the large-scale motion 267 from the video stream 120 using the breathing model 283. The method 650 may be performed by the system 100 and/or processing apparatus 405.

The method 650 starts, and in one embodiment, the processing apparatus 405 trains 651 the breathing model 283 on training video streams 120 of a plurality of subjects 110. In one embodiment, the video streams 120 are presented to the input neurons 450 of the neural network 475. In a certain embodiment, the training 651 is supervisory training with the large-scale motion 267 and/or a breathing signal 183 being specified for each video stream 120.

The processing apparatus 405 further receive 653 a video stream 120 of the subject 110 in a non-training situation. For example, the video stream 120 may be of a sleeping child. The processing apparatus 405 estimates 655 the breathing signal 183 from the video stream 120 using the breathing model 283. In one embodiment, the processing apparatus 405 presents the video stream 120 to the breathing model 283 and receives the breathing signal 183 as an output of the breathing model 283.

The processing apparatus 405 further determines 657 the large-scale motion 267 from the video stream 120 using the breathing model 283 and the method 650 ends. In one embodiment, the processing apparatus 405 presents the video stream 120 to the breathing model 283 and receives the large-scale motion 267 as an output of the breathing model 283.

Figure 5D:
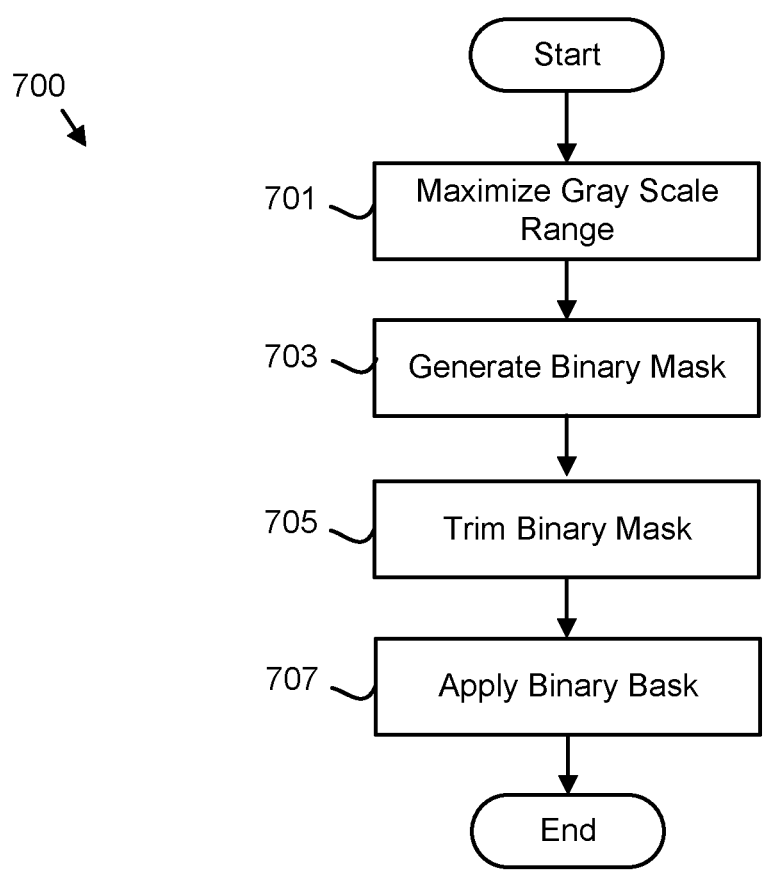
FIG. 5D is a schematic flow chart diagram illustrating one embodiment of a masking method.

FIG. 5D is a schematic flow chart diagram illustrating one embodiment of a masking method 700. The method 700 generates and applies a binary mask 320 to image frames 5 and/or removed frames 7 of the video stream 120. The method 700 may be performed by the system 100 and/or processing apparatus 405.

The method 700 starts, and in one embodiment, the processing apparatus 405 maximizes 701 a grayscale range of a first image frame 5 and/or first removed frame 7 using a contrast correction and/or a gamma correction. The processing apparatus 405 further generates 703 the binary mask 320 by applying an edge detector to the first image frame 5 and/or removed frame 7. In one embodiment, the edge detector is a Sobel edge detector.

The processing apparatus 405 may trim 705 the binary mask 320 to accept a maximum number of values. In one embodiment, areas of an image frame 5 and/or removed frame 7 that are not likely to contain the subject 110 are indicated by the binary mask 320. As a result, the areas indicated by the binary mask 320 may not be processed. The processing apparatus 405 may apply 707 the binary mask 320 to subsequent image frames 5 and/or removed frames 7 and the method 700 ends.

Figure 5E:
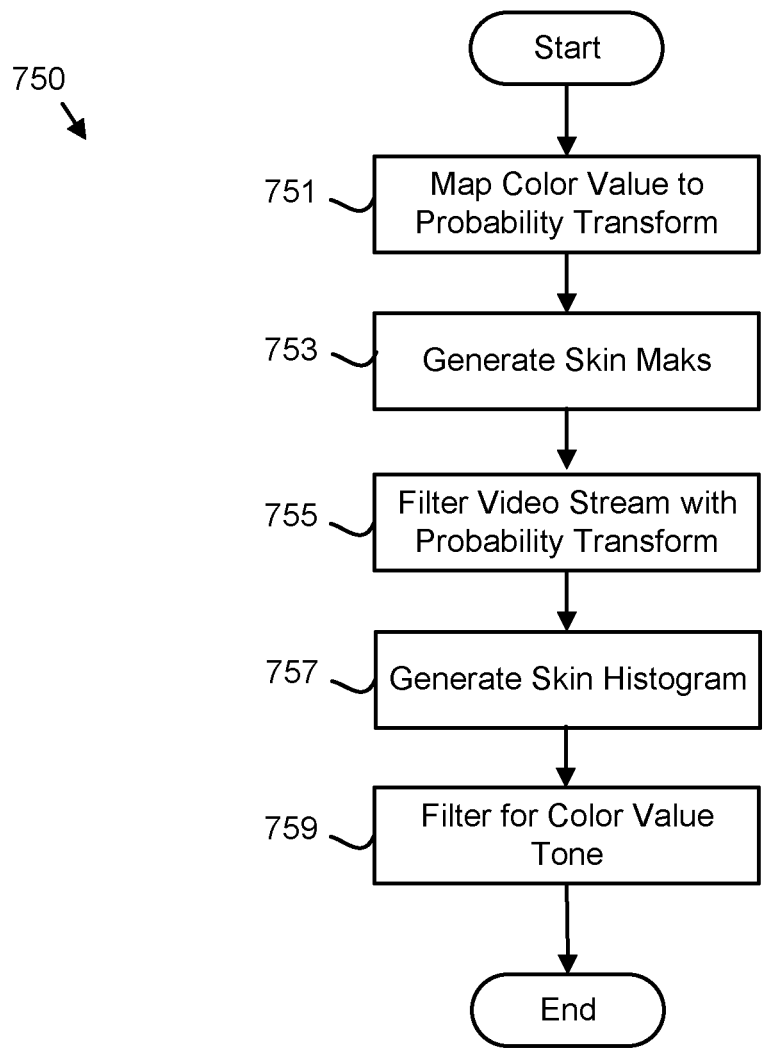
FIG. 5E is a schematic flow chart diagram illustrating one embodiment of a face filtering method.
Figure 5F:
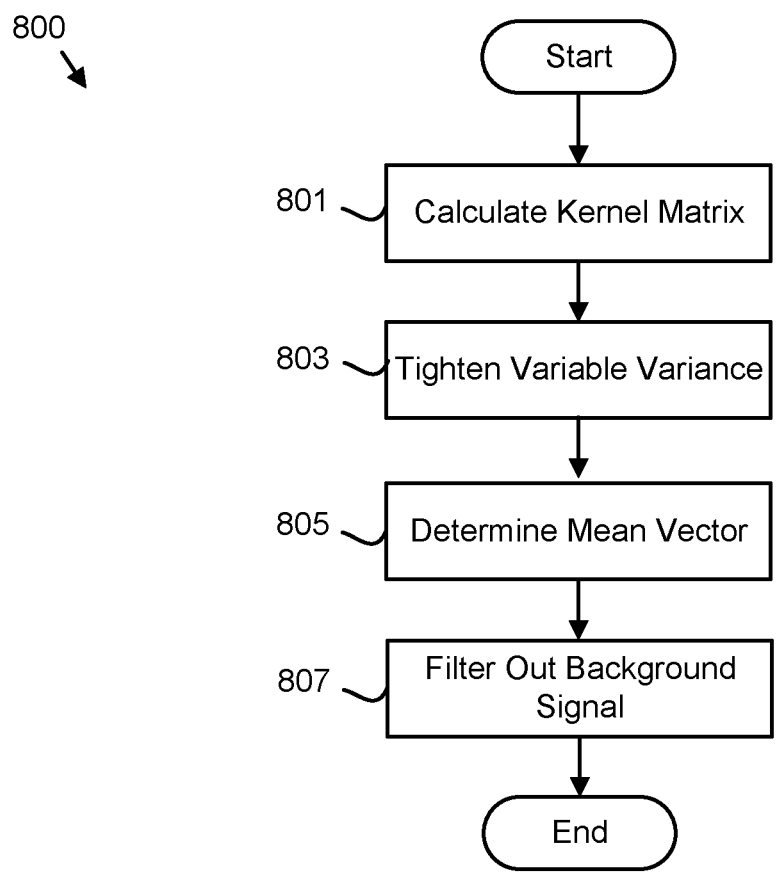
FIG. 5F is a schematic flow chart diagram illustrating one embodiment of a background signal filtering method.
Figure 5G:
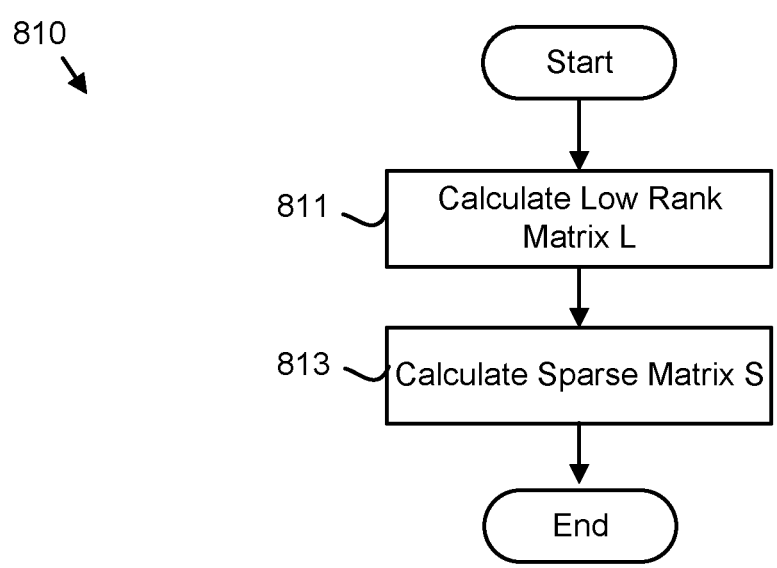
FIG. 5G is a schematic flow chart diagram illustrating one embodiment of a moving object identification method.

FIG. 5E is a schematic flow chart diagram illustrating one embodiment of a face filtering method 750. The method 750 filters for a face of the subject 110 based on one or more color values 327. The method 750 may be performed by the system 100 and/or processing apparatus 405.

The method 750 starts, and in one embodiment, the processing apparatus 405 map 751 maps each color value 327 to a probability transform 329 that the color value 327 corresponds to skin of the subject 110. The processing apparatus 405 further generates 753 the skin mask 325. In one embodiment, the processing apparatus 405 generates 753 the skin mask 325 by applying the probability transform 329 during an initialization. For example, the probability transform 329 may be applied to each pixel 9 of an image frame 5 and/or removed frame 7. Pixels 9 and/or color values 327 that correspond to skin of the subject 110 are indicated by the probability transform 329. In one embodiment, most likely color values 327 are identified from the skin histogram 326.

The processing apparatus 405 may filter 755 the video stream 120 with one or more probability transforms 329 during the initialization. In addition, the processing apparatus 405 may generate 757 the skin histogram 326 from the filtered video stream 120 during the initialization. In one embodiment, the processing apparatus 405 identifies a color value 327 based on the skin histogram 326. The color value 327 may be most common color values 327. The processing apparatus 405 may filter 759 each image frame 5 and/or removed frame 7 to retain the color value 327 and corresponding pixels 9 and the method 750 ends.

FIG. 5F is a schematic flow chart diagram illustrating one embodiment of a background signal filtering method 800. The method 800 filters out a background signal 333 with the background signal filter 335. The method 800 may be performed by the system 100 and/or processing apparatus 405.

The method 800 starts, and in one embodiment, the processing apparatus 405 calculates 801 the Kernel matrix 330 from sampled points of the video stream 120 with a variable variance. The processing apparatus 405 may further tighten 803 the variable variance of the kernel matrix 330 in response to detecting motion in the video stream 120. The processing apparatus 405 may determine 805 the mean vector 331. The mean vector 331 may be generated from the kernel matrix 330. In one embodiment, the mean vector 331 is the background signal 333. The processing apparatus 405 may employ the background signal filter 335 to filter 807 the background signal 333 from the video stream 120 and the method 800 ends.

FIG. 5G is a schematic flow chart diagram illustrating one embodiment of a moving object 150 identification method 810. The method 810 may filter nonmoving objects 151 from an image frame 5 to yield the removed frame 7 with moving objects 150. The method 810 may be performed by the system 100 and/or processing apparatus 405.

The method 810 starts, and in one embodiment, the processing apparatus 405 calculates 811 the low rank matrix L 135 representing the nonmoving objects 151. In a certain embodiment, the low rank matrix L 135 is calculated as a matrix of joint probability estimations. The joint probability estimations may be calculated using a Kalman filter.

The processing apparatus 405 further calculates 813 the sparse matrix S 130 representing the moving objects 150 by removing the low rank matrix L 135 from matrix X 125 and the method 810 ends. As a result, sparse matrix S 130 represents the moving objects 150.

Figure 6A:
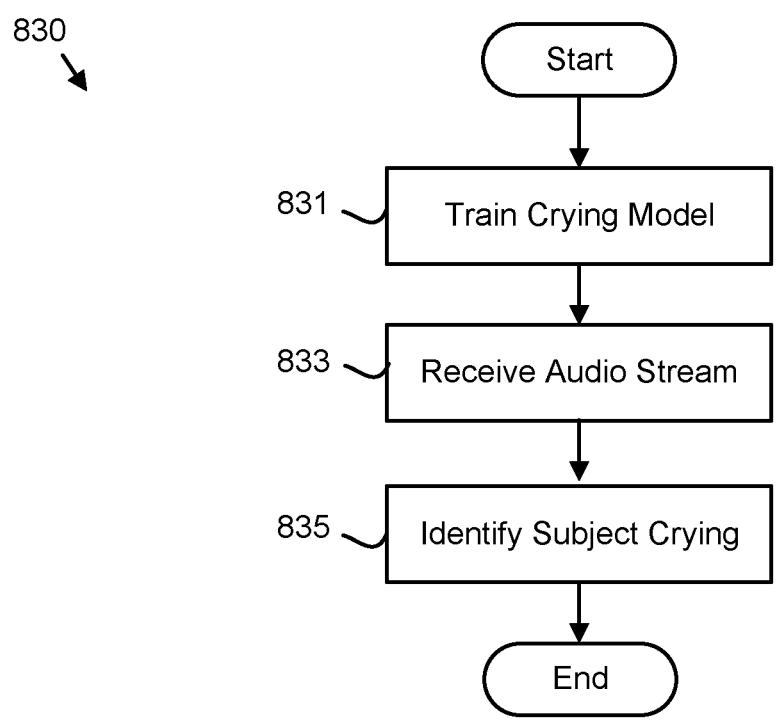
FIG. 6A is a schematic flow chart diagram illustrating one embodiment of a crying identification method.

FIG. 6A is a schematic flow chart diagram illustrating one embodiment of a crying identification method 830. The method 830 may identify a crying subject 110. The method 830 may be performed by the system 100 and/or processing apparatus 405.

The method 830 starts, and in one embodiment, the processing apparatus 405 trains 831 the crying model 285 on a plurality of subjects 110 crying. The crying model 285 may be trained 831 on audio streams 131 of subjects 110 identified as crying, and not crying. In one embodiment, the crying audio streams 131 are identified as hungry, distressed, sleepy, and likely to fall asleep.

The processing apparatus 405 further receives 853 an audio stream 131 from a given subject 110. The processing apparatus 405 identifies 835 whether the given subject 110 is crying from the audio stream 131 using the crying model 285 and the method 830 ends. The audio stream 831 may be applied to the input neurons 450 of the neural network 475 to generate an indication that the given subject 110 is crying or not crying at the output neurons 860. In one embodiment, crying is identified as hungry, distressed, sleepy, and likely to fall asleep by the output neurons 860.

Figure 6B:
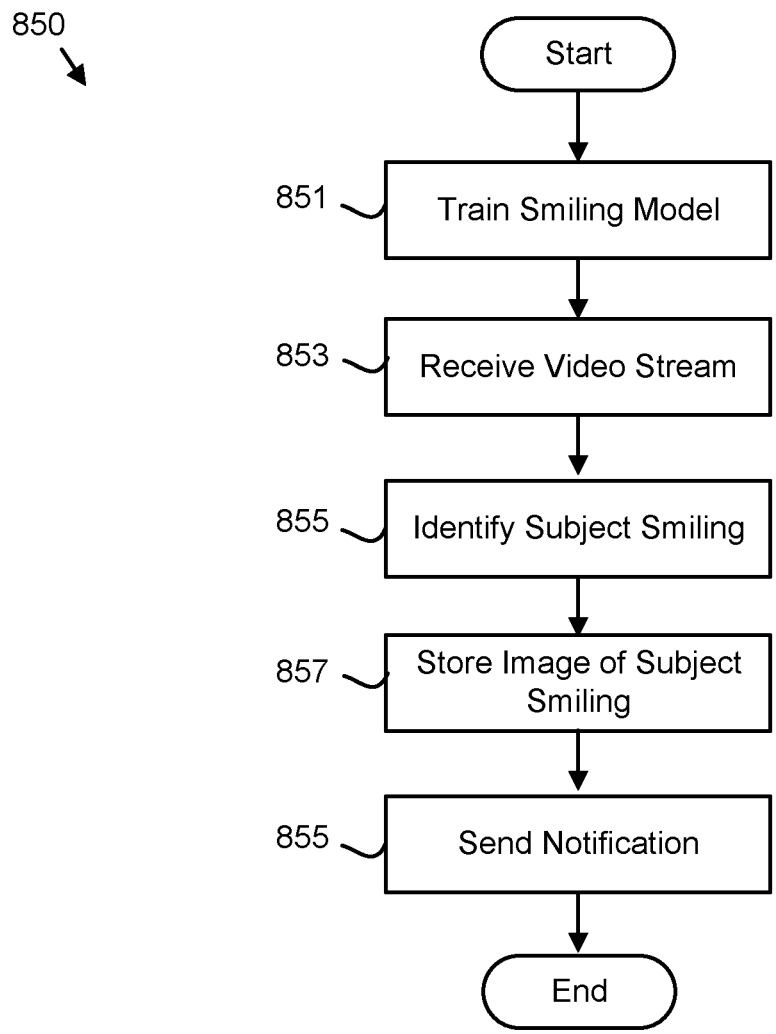
FIG. 6B is a schematic flow chart diagram illustrating one embodiment of a smiling identification method.

FIG. 6B is a schematic flow chart diagram illustrating one embodiment of a smiling identification method 850. The method 850 identifies a subject 110 smiling. In addition, the method 850 may send a notification 291 with the smiling image 289. The method 830 may be performed by the system 100 and/or processing apparatus 405.

The method 850 starts, and in one embodiment, the processing apparatus 405 trains 851 the smiling model 287 on a plurality of subjects 110 smiling. The smiling model 287 may be trained 851 by presenting a plurality of video streams 120 of subjects 110 that are smiling or not smiling to the input neurons 450. In supervised training, each video stream 120 may be identified 855 as smiling or not smiling.

The processing apparatus 405 may further receive 853 a video stream 120 of a given subject 110. The processing apparatus 405 may present the video stream 120 to the smiling model 287. In one embodiment, the video stream 120 is presented to the input neurons 450. The processing apparatus 405 may identify 855 the given subject smiling using the smiling model 287. An indication that the given subject 110 is smiling or not smiling may be received from the output neurons 460.

The processing apparatus 405 may store 857 the smiling image 289 of the subject smiling in response to detecting the subject 110 smiling. In one embodiment, the processing apparatus 405 sends 855 a notification 291 comprising the smiling image 289 in response to detecting the subject 110 smiling and the method 850 ends.

Figure 6C:
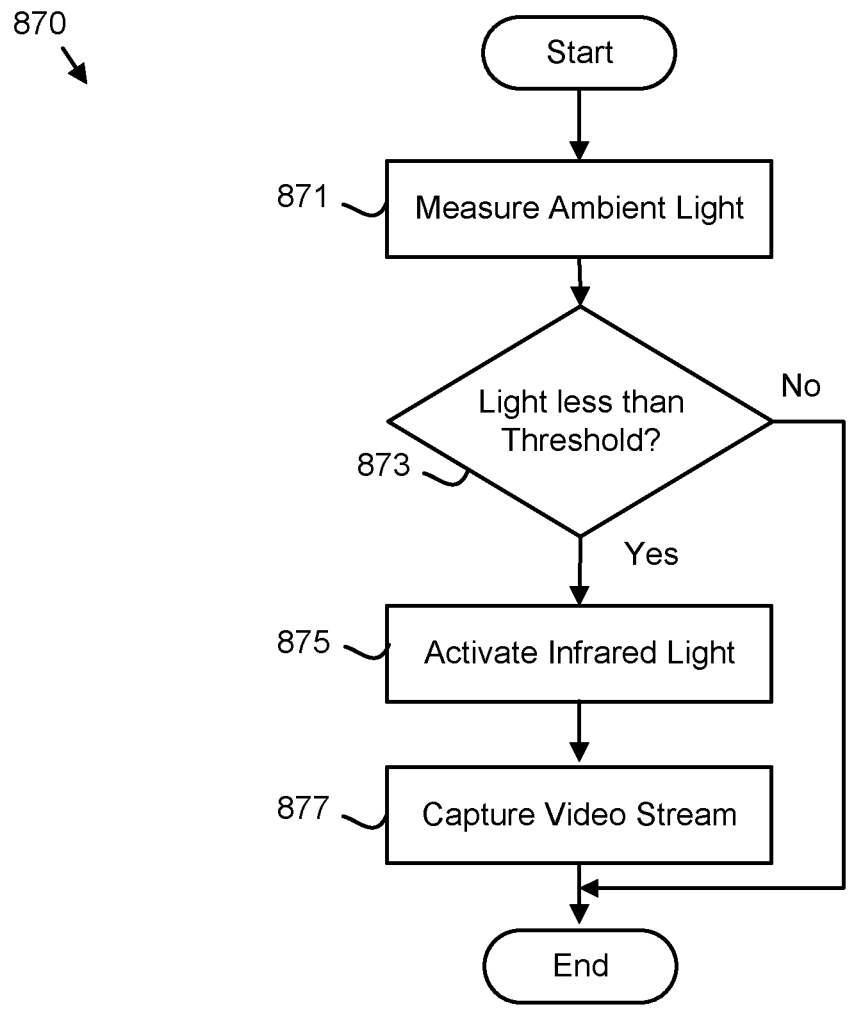
FIG. 6C is a schematic flow chart diagram illustrating one embodiment of an infrared light activation method.

FIG. 6C is a schematic flow chart diagram illustrating one embodiment of an infrared light activation method 870. The method 870 may activate the infrared light 129. The method 870 may be performed by the system 100 and/or processing apparatus 405.

The method 870 starts, and in one embodiment, the processing apparatus 405 measures 871 the ambient light. The processing apparatus 405 may employ the camera 105 to measure 871 the ambient light. The processing apparatus 405 further determines 873 if the ambient light is less than a light threshold. In response to the ambient light being less than the light threshold, the processing apparatus 405 activates 875 the infrared light 129. The processing apparatus 405 and/or camera 105 may capture 877 the video stream 120 using the illumination from the infrared light 129 and the method 870 ends. The video stream 120 may capture 877 the subject 110 in infrared.

Figure 6D:
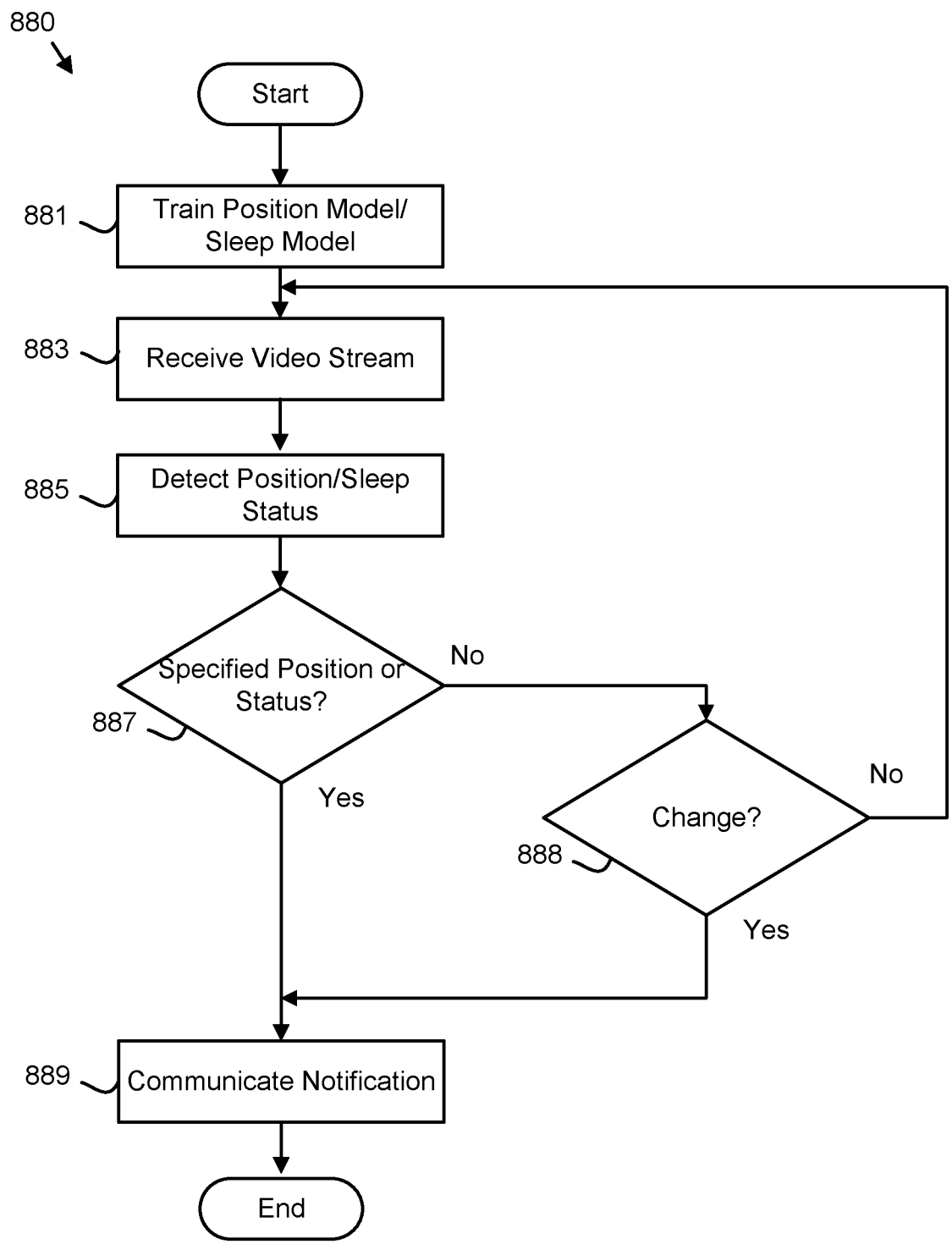
FIG. 6D is a schematic flow chart diagram illustrating one embodiment of a status change notification method.

FIG. 6D is a schematic flow chart diagram illustrating one embodiment of a status change notification method 880. The method 880 detects a position and/or sleep status and/or a change in position and/or sleep status of a subject 110 The method 880 may be performed by the system 100 and/or processing apparatus 405.

The method 880 starts, and in one embodiment, the processing apparatus 405 trains 881 the position model 293. In addition, the processing apparatus 405 may train 881 the sleep model 295. The processing apparatus 405 may present a plurality of video streams 120 and/or image frames 5 to neural networks 475 for the position model 293 and/or sleep model 295. The sleep position 341 and/or sleep status 343 for each video stream 120 and/or image frame 5 may be identified. The trained position model 293 may generate a sleep position 341 in response to a video stream 120. The trained sleep model 295 may generate a sleep status 343 in response to a video stream 120.

The processing apparatus 405 further receives 883 of video stream 120 for a given subject 110. The processing apparatus 405 may detect 885 the sleep position 341 and/or sleep status 343. The sleep position 341 and/or sleep status 343 may be detected 285 using the position model 293 and the sleep model 295 respectively.

The processing apparatus 405 determines 887 whether the sleep position 341 is a specified sleep position 341. For example, the specified sleep position 341 may be a back orientation. In addition, the processing apparatus 405 determines 887 whether the sleep status 343 is a specified sleep status 343. For example, the specified sleep status 343 may be awake.

If the sleep position 341 is the specified sleep position 341 and/or the sleep status 343 is the specified sleep status 343, the processing apparatus 405 communicates a notification 291. The notification 291 may indicate the specified sleep position 341 and/or specified sleep status 343. If the sleep position 341 is not the specified sleep position 341 and the sleep status 343 is not the specified sleep status 343, the processing apparatus 405 determines 888 if there is a change in the sleep position 341 and/or sleep status 343. The change may be relative to a previous sampling period. If no changes determined 888, the processing apparatus 405 continues to receive 883 the video stream 120. If the change of sleep position 341 and/or a change of sleep status 343 is determined 888, the processing apparatus 405 communicates 889 the notification 291 and the method 880 ends. The notification 291 may indicate the change of the sleep position 341 and/or the change of the sleep status 343.

Figure 6E:
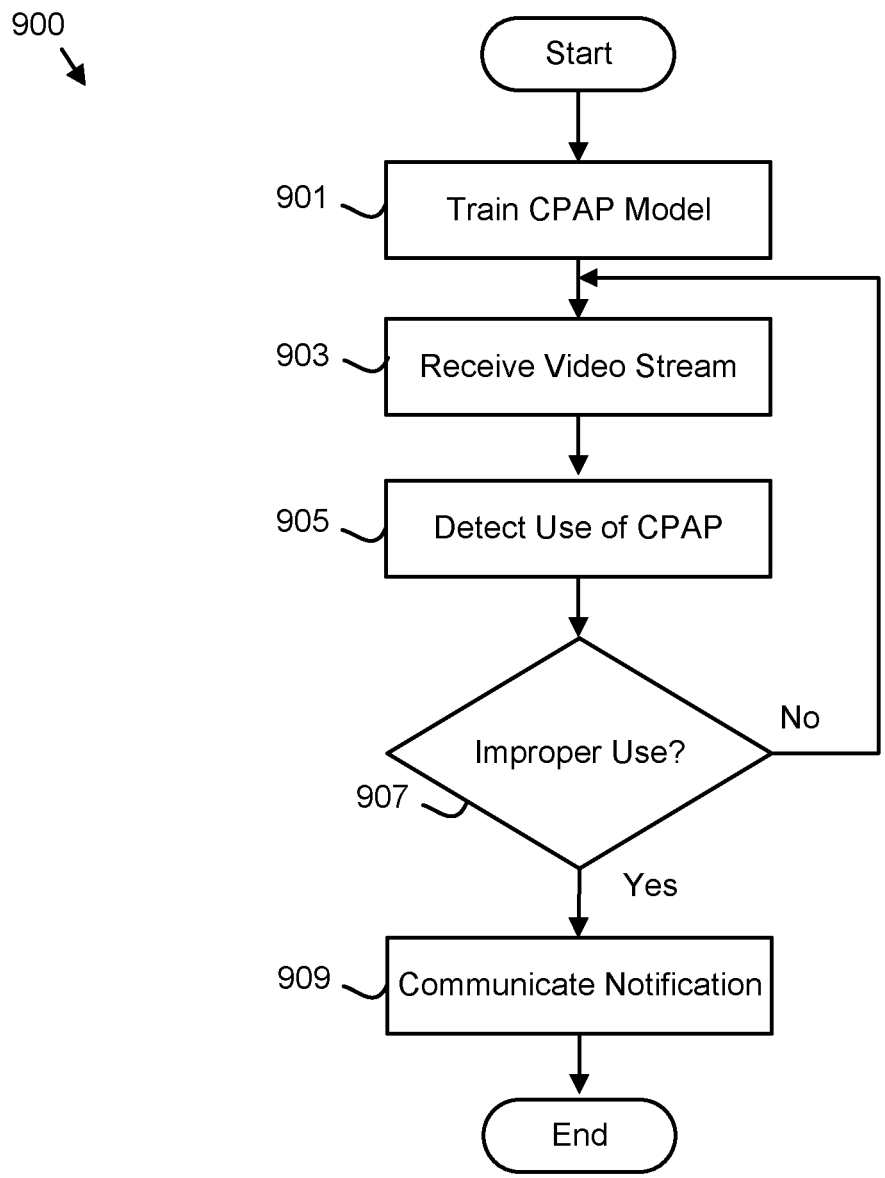
FIG. 6E is a schematic flow chart diagram illustrating one embodiment of a CPAP notification method.

FIG. 6E is a schematic flow chart diagram illustrating one embodiment of a CPAP notification method 900. The method 900 may detect improper use of a CPAP machine and communicated notification 291. The method 900 may be performed by the system 100 and/or processing apparatus 405.

The method 900 starts, and in one embodiment, the processing apparatus 405 trains 901 the CPAP model 297. The processing apparatus 405 may present a plurality of video streams 120 and/or frame images 5 to the neural network 475. Some of the video streams 120 and/or frame images 5 may include CPAP machines while others do not. The processing apparatus 405 may identify the video streams 120 and/or frame images five that include CPAP machines to train the neural network 475 and/or CPAP model 297.

The processing apparatus 405 further receives 903 a video stream 120 of the subject 110. The processing apparatus 405 may detect 905 use of the CPAP machine. In one embodiment, the processing apparatus 405 presents the video stream 120 to the CPAP model 297 and the CPAP model 297 indicates if the CPAP machine is in use.

The processing apparatus further detects 907 improper use of the CPAP machine. In one embodiment, the processing apparatus 405 presents the video stream 120 to the CPAP model 297. The CPAP model 297 indicates whether the CPAP machine is being used improperly. If no improper use is detected 907, the processing apparatus 405 continues to receive 903 the video stream 120. If improper use is detected 907, the processing apparatus 405 communicates 909 a notification 291 of the improper use and the method 900 ends. The notification 291 may describe the improper use.

Figure 6F:
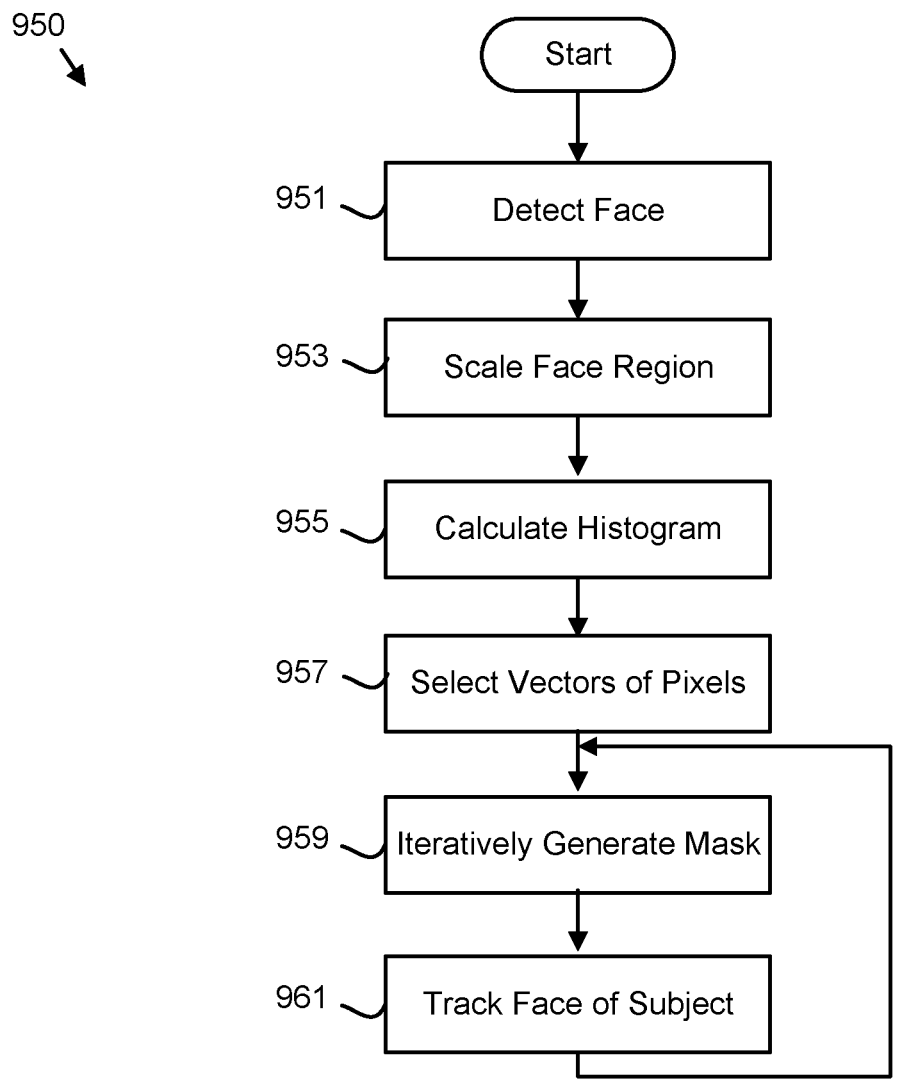
FIG. 6F is a schematic flow chart diagram illustrating one embodiment of a motion tracking method.

FIG. 6F is a schematic flow chart diagram illustrating a motion tracking method 950. The method 950 may track a subject 110. The method 900 may be performed by the system 100 and/or processing apparatus 405.

The method 950 starts, and in one embodiment, the processing apparatus 405 detects 951 the face of the subject 110. A face detection algorithm may be employed. The processing apparatus 405 may scale 953 a face region 337 comprising the face to a specified pixel size. The specified pixel size may be in the range of 32 to 256 pixels squared. In a certain embodiment, the specified pixel size is 64 pixels squared.

The processing apparatus 405 further calculates 955 a skin histogram 326 on the color space of the face region 337 comprising the face. The skin histogram 326 may bin pixels 9 of the face based on a color value 327 such as a 24-bit color. In a certain embodiment, pixels of the face region 337 are binned based on the color values 327. In one embodiment, a specified bin number of bins are employed. The specified bin number of bins may be in the range of 8 to 24 bins. In one embodiment, 12 bins are employed.

The processing apparatus 405 may select 957 vectors of pixels 9 for the binary mask 320 and/or the skin mask 325 from the bins of the skin histogram 326 with the highest counts. The vectors of pixels 9 may be used to iteratively generate 959 subsequent binary masks 320 and/or skin masks 325 that are used to track the face of the subject 110. The binary masks 320 and/or skin masks 325 may track the face.

The processing apparatus 405 iteratively tracks 961 the face of the subject 110. In one embodiment, the processing apparatus 405 generates a N by N by 4 image X, where N is the specified size of the face region. The processing apparatus 405 further updates the binary mask 320 and/or skin mask 325 as described below.

The processing apparatus 405 may apply a cosine-shaped taper window W to X. This operation is performed in-place as X←W⊙X, where ⊙ implies element by element multiplication of W applied to each for the four color planes in X. Application of the taper window enforces smoothness and periodicity assumptions made when exploiting the circular shift property of a Fast Fourier transform (FFT). The FFT is used for computational efficiency.

The processing apparatus 405 may further compute the 2-dimensional FFT of X and compute the 2-dimensional FFT for Z where Z is an N by N by 4 appearance model that is updated as described below. The processing apparatus 405 may evaluate a Gaussian kernel function matrix K, as K=k(Xf,Zf) where k is a Gaussian function. The processing apparatus 405 may compute a 2-dimensional FFT, KfFFT2(K), and compute kernel coefficients in frequency domain, fAfBf, where Af and Bf are updated as described below. The processing apparatus 405 may compute a response R in the frequency domain: RffKf, and compute the response in the spatial domain, RIFFT2(Rf). The processing apparatus 405 may determine the maximum of the response in the spatial domain, (xmax,ymax) and subtract the response from the image center to find the estimated change in object position (x,y) in tracker coordinates. The processing apparatus 405 may scale to image coordinates and add to an estimated object position to obtain the updated estimate of the object position. The processing apparatus 405 may extract a new image X from the image at the updated estimate of the object position.

The processing apparatus 405 may iteratively calculate the 2-dimensional FFT of X, XfFFT2(X) and evaluate the Gaussian kernel function matrix K where Kk(Xf,Xf). The processing apparatus 405 further calculates the 2-dimensional FFT KfFFT2(K). The processing apparatus 405 calculates an updated numerator, Af(1−)Af+KfYf, where Yf is a Gaussian target function. In addition, the processing apparatus 405 calculates an updated denominator, Bf(1−)Bf+ (Kf+). The processing apparatus 405 further calculates the updated appearance models, Z(1−)Z+X. The processing apparatus 405 then calculates the 2-dimensional FFT of X, XfFFT2(X) and evaluates the Gaussian kernel function matrix K where Kk(Xf,Xf), repeating the iterative calculation.

The embodiments efficiently detect the breathing event 265 and/or large-scale motion 267 from the video stream 120 and generate an alert of neither the breathing event 265 or large-scale motion 267 is detected. As a result, the subject 110 may be rendered timely aid if the subject 110 stops breathing or moving.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A method comprising:
training, by a processing apparatus, a breathing model on training video streams of a plurality of subjects;
receiving, by the processing apparatus, a first video stream of a subject;
estimating, by the processing apparatus, a breathing signal from the first video stream using the breathing model;
determining, by the processing apparatus, one of a large-scale motion and/or a breathing event of the subject based on the breathing signal using the breathing model;

generating, by the processing apparatus, an alert if both no breathing event is identified and no large-scale motion of the subject is identified within an event time interval;
presenting, by the processing apparatus, the first video stream, a breathing report, and/or an audio stream, wherein the breathing report comprises a numerical representation, a heat map, a graph, and/or a streaming sinusoidal graph of a breath rate, a maximum inter-breath interval, a minimum inter-breath interval, inter-breath interval statistics, and inter-breath interval histogram, motion frequency, motion magnitude, motion duration, sleep length, sleep quality, sleep intervals, a sleep position, a sleep status, and/or apnea event data;
detecting, by a processing apparatus, a sleep position and/or a sleep status of the subject from the first video stream, wherein the sleep position comprises thrashing, a stomach orientation, a back orientation, and/or a side orientation and the sleep status comprises asleep and awake; and
communicating, by the processing apparatus, a notification in response to a specified sleep position, a specified sleep status, a change of the sleep position, and/or a change of sleep status.

2. The method of claim 1, the method further comprising:
training, by a processing apparatus, a crying model on a plurality of subjects crying;
receiving, by the processing apparatus, an audio stream; and
identifying, by the processing apparatus, the subject crying from the audio stream using the crying model.

3. The method of claim 1, the method further comprising:
training, by a processing apparatus, a smiling model on a plurality of subjects smiling; and
identifying, by the processing apparatus, the subject smiling from the first video stream using the smiling model.

4. The method of claim 1, the method further comprising:
measuring, by a processing apparatus, ambient light; and
in response to the ambient light being less than a light threshold, activating, by the processing apparatus, an infrared light, wherein the first video stream captures the subject in infrared.

5. The method of claim 1, the method further comprising:
detecting, by the processing apparatus, a face from the first video stream;
scaling, by the processing apparatus, a face region comprising the face to a specified pixel size;
calculating, by the processing apparatus, a skin histogram on a color space of face region;
selecting, by the processing apparatus, vectors of pixels based on the skin histogram;
iteratively generating, by the processing apparatus, a skin mask from the vectors; and
iteratively tracking, by the processing apparatus, the face.

6. An apparatus comprising:
a processing apparatus;
a memory storing code executable by the processing apparatus to perform:
training a breathing model on training video streams of a plurality of subjects;
receiving a first video stream of a subject;
estimating a breathing signal from the first video stream using the breathing model;
determining one of a large-scale motion and/or a breathing event of the subject based on the breathing signal using the breathing model;
generating an alert if both no breathing event is identified and no large-scale motion of the subject is identified within an event time interval;
presenting the first video stream, a breathing report, and/or an audio stream, wherein the breathing report comprises a numerical representation, a heat map, a graph, and/or a streaming sinusoidal graph of a breath rate, a maximum inter-breath interval, a minimum inter-breath interval, inter-breath interval statistics, and inter-breath interval histogram, motion frequency, motion magnitude, motion duration, sleep length, sleep quality, sleep intervals, a sleep position, a sleep status, and/or apnea event data;
detecting a sleep position and/or a sleep status of the subject from the first video stream, wherein the sleep position comprises thrashing, a stomach orientation, a back orientation, and/or a side orientation and the sleep status comprises asleep and awake; and
communicating a notification in response to a specified sleep position, a specified sleep status, a change of the sleep position, and/or a change of sleep status.

7. The apparatus of claim 6, the processing apparatus further:
training a crying model on a plurality of subjects crying;
receiving an audio stream; and
identifying the subject crying from the audio stream using the crying model.

8. The apparatus of claim 6, the processing apparatus further:
training a smiling model on a plurality of subjects smiling; and
identifying the subject smiling from the first video stream using the smiling model.

9. The apparatus of claim 6, the processing apparatus further:
measuring ambient light; and
in response to the ambient light being less than a light threshold, activating an infrared light, wherein the first video stream captures the subject in infrared.

10. The apparatus of claim 6, the processing apparatus further:
detecting a face from the first video stream;
scaling a face region comprising the face to a specified pixel size;
calculating a skin histogram on a color space of face region;
selecting vectors of pixels based on the skin histogram;
iteratively generating a skin mask from the vectors; and
iteratively tracking the face.

11. A system comprising:
a camera;
a processing apparatus;
a memory storing code executable by the processing apparatus to perform:
training a breathing model on training video streams of a plurality of subjects;
receiving a first video stream from the camera of a subject;
estimating a breathing signal from the first video stream using the breathing model;
determining one of a large-scale motion and/or a breathing event of the subject based on the breathing signal using the breathing model;
generating an alert if both no breathing event is identified and no large-scale motion of the subject is identified within an event time interval;

presenting the first video stream, a breathing report, and/or an audio stream, wherein the breathing report comprises a numerical representation, a heat map, a graph, and/or a streaming sinusoidal graph of a breath rate, a maximum inter-breath interval, a minimum inter-breath interval, inter-breath interval statistics, an inter-breath interval histogram, motion frequency, motion magnitude, motion duration, sleep length, sleep quality, sleep intervals, a sleep position, a sleep status, and/or apnea event data;

detecting a sleep position and/or a sleep status of the subject from the first video stream, wherein the sleep position comprises thrashing, a stomach orientation, a back orientation, and/or a side orientation and the sleep status comprises asleep and awake; and communicating a notification in response to a specified sleep position, a specified sleep status, a change of the sleep position, and/or a change of sleep status.

12. The system of claim 11, the processing apparatus further:

training a crying model on a plurality of subjects crying;
receiving an audio stream; and
identifying the subject crying from the audio stream using the crying model.

13. The system of claim 11, the processing apparatus further:

training a smiling model on a plurality of subjects smiling; and
identifying the subject smiling from the first video stream using the smiling model.

14. The system of claim 11, the processing apparatus further:

measuring ambient light; and
in response to the ambient light being less than a light threshold, activating an infrared light, wherein the first video stream captures the subject in infrared.

15. The system of claim 11, the processing apparatus further:

detecting a face from the first video stream;
scaling a face region comprising the face to a specified pixel size;
calculating a skin histogram on a color space of face region;
selecting vectors of pixels based on the skin histogram;
iteratively generating a skin mask from the vectors; and
iteratively tracking the face.

* * * * *